(12) United States Patent  
Chen

(10) Patent No.: US 6,794,399 B2
(45) Date of Patent: Sep. 21, 2004

(54) 1,4-DIHYDROPYRIDINE DERIVATIVE WITH A GUAIACOXYPROPANOLAMINE AND/OR PHENOXYPROPANOLAMINE MOIETY

(76) Inventor: Ing-Jun Chen, 10F, No. 148-95, Guang-Hwa 1st Rd., Kaohsiung (TW)

(*) Notice: Subject to any disclaimer, the term of this patent is extended or adjusted under 35 U.S.C. 154(b) by 0 days.

(21) Appl. No.: 10/119,709

(22) Filed: Apr. 11, 2002

(65) Prior Publication Data

US 2002/0156109 A1 Oct. 24, 2002

Related U.S. Application Data

(63) Continuation of application No. 09/347,763, filed on Jul. 6, 1999, now abandoned.

(30) Foreign Application Priority Data

Jul. 21, 1998 (CN) .......................................... 87111827 A

(51) Int. Cl.[7] .................. A61K 31/4418; C07D 213/46
(52) U.S. Cl. ..................... 514/356; 514/356; 546/321
(58) Field of Search ........................ 514/356; 546/321

(56) References Cited

PUBLICATIONS

Jhy–Chong Liang, et al, "Labedipinedilol–A: . . . ", Drug Development Research, 2000, Wiley–Liss, Inc., vol. 49, pp. 94–108.*

(List continued on next page.)

*Primary Examiner*—Alan L. Rotman
*Assistant Examiner*—Janet L Coppins
(74) *Attorney, Agent, or Firm*—Birch, Stewart, Kolasch & Birch, LLP

(57) ABSTRACT

The invention disclosed some 1,4-dihydropiridine derivative chemically with guaiacoxypropanolamine based phenoxypropanolamine moiety and pharmacologically with β-adrenoceptor blocking and partial β$_2$-agonist activities, is now emerging.

The compound of 1,4-dihydropiridine derivative wherein has the formula I,

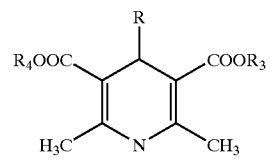

wherein R selected from four group as follow

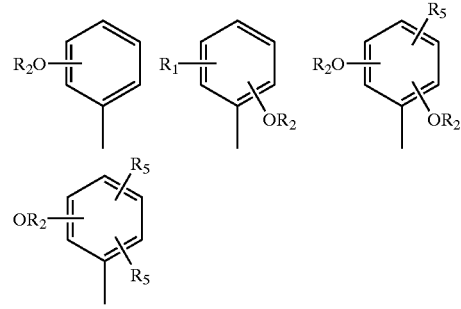

$R_1$ selected from X, H, $NO_2$ saturated $C_1$–$C_6$ alkyl chain, unsaturated $C_6$–$C_6$ alkyl chain, $R_2$ selected from H, $CH_3$

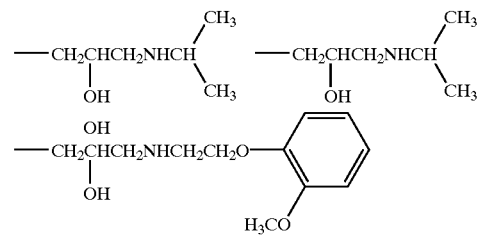

$R_3$ and $R_4$ are individually selected from saturated $C_1$–$C_6$ alkyl chain, unsaturated $C_1$–$C_6$ alkyl chain; $R_5$ selected from OH, saturated $C_1$–$C_6$ alkyl chain, unsaturated $C_1$–$C_6$ alkyl chain.

5 Claims, 49 Drawing Sheets

YM430

YM1615-1

PUBLICATIONS

CA 94:167456, Baldwin et al. 1981.*
CA 84:150511, Ger. offen 2,405,658 1976.*
CA 116:173968, Yan et al 1992.*
CA 135:282947, Yeh et al. 2001.*
CA 133:68681, Liang et al. 2000.*
CA 132:137107, Chen 2000.*

* cited by examiner

YM430

YM1615-1

1,4-DIHYDROPYRIDINE DERIVATIVE WITH A GUAIACOXYPROPANOLAMINE AND/OR PHENOXYPROPANOLAMINE MOIETY

This application is a continuation of application No. 09/347,763, filed on Jul. 6, 1999, now abandoned, which claims priority to Republic of China application number 87111827, filed on Jul. 21, 1998.

BACKGROUND OF THE INVENTION

1. Field of Applications

This invention which could continuously maintain hypotension; with activation of competitive β-adrenoreceptor and calcium channel blocking agent; induced vasorelaxing effect; with calcium channel antagonist and β-adrenoreceptor antagonist activity, is a series of 1,4-dihydropiridine derivatives chemically with guaiacoxypropanolamine and/or phenoxypropanolamine moiety.

2. Background of the Invention

Serious and pernicious hypertensive subjects could obtain rapid hypotension by treatment with nifedipine, yet too rapid or strong effect could result in tachycardia. In later experiments, it is found that while administrating vasodilator, provision of β-adrenoceptor blocking agent to subjects could inhibit tachycardia induced by sympathetic excitation. Clinical reports have shown that in the treatment of angina pectoris and hypertension, combination therapy of, β-adrenoceptor blocking agent and calcium entry blocking agent has advantage efficacy over any one of those drugs (Fitzsimons, T. J., *J. Hypertens.*, 5, pp. S11-S15, 1987).

In most original hypertension subjects, their peripheral circulation usually have a much higher resistance than normal. Though directly effective vasodilator could reduce the resistance, therefore these drugs could induce unwanted effects, including reflex tachycardia due to baroreceptor activation which may impair the hypotensive effect by blood vessel contraction; tachycardia; increase of cardiac output. Some reports have already pointed out that β-adrenoceptor blocking agent could inhibit tachycardia due to sympathetic excitation after administration of vasodilator.

Nifedipine is a peripheral vasodilator with 1,4-dihydropiridine ring. It is effective on the cardiac blood vessels, including vasodilatation, where it functions by directly inhibit the result of calcium ion inflow in vessel's smooth muscle cell membrane. Theoretically, combination therapy of calcium entry blocking agent and β-adrenoceptor blocking agent may result in two different cardiac suppression effect. Nevertheless, reports have demonstrated that though nifedipine would increase the heart rate and renin level in hypertensive subjects, these effects could be inhibited by concurrent administration of PROPRANOLOL. Furthermore, it has been observed that there is coordinating effect of this combination therapy in lowering the blood pressure.

DESCRIPTION OF THE PRIOR ART

To overcome the tachycardia tendency due to the direct effect of peripheral vasodilator, the inventor has tried designing a chemical compound which has both vasodilatation and, β-adrenoceptor blocking agent activation effects. VANIDILOL, previously described as a β-blocking agent, is chemically with a guaiacoxypropanolamines moiety, while this synthesized vanidipinedilol of this inventor, which belongs to the derivative of VANIDILOL, has been demonstrated in a series of experiment and indicates that it has both β-adrenoceptor blocking and added calcium channel blocking effects.

Furthermore, Asano, M. (*J. Pharmacol*, 296, pp. 204–211, 1990) has suggested YM-16151-1, and Shibasaki, K. (*Gen. Pharmac.* 29, pp. 545–550, 1997) has demonstrated YM 430. Though both these two compounds have β-adrenoceptor blocking effects as shown in FIG. 1, their structures are different from this invention.

SUMMARY OF THE INVENTION

Therefore, this invention will attempt to undergo structural embellishment, using VANIDILOL as the fundamental key structure. The main purpose is to embellish aldehyde at the 4 position on VANIDILOL, and introduce a dihydropyridine ring that with vasodilatation effect.

This invention will also make use of various pharmacological experiments to demonstrate that these 1,4-dihydropiridine derivatives chemically with guaiacoxypropanolamine and/or phenoxypropanolamine moiety could continuously maintain hypotension; with activation of competitive β-adrenoreceptor and calcium channel blocking agent; induced vasorelaxing effect; and with activation of calcium channel antagonist and, β-adrenoreceptor antagonist.

This invention will further demonstrate that by having 1,4-dihydropiridine derivative chemically with guaiacoxypropanolamine or phenoxypropanolamine moiety as the main component and adding necessary excipients to form various pharmacological compounds that is therapeutically efficient.

BRIEF DESCRIPTION OF THE DRAWINGS

Table 1 The effect of this invention compound on heart rate and hypertensive.

Table 2 This invention compound and its $pA_2$ value.

Table 3 This invention compound and its pKi value.

Figure 1:
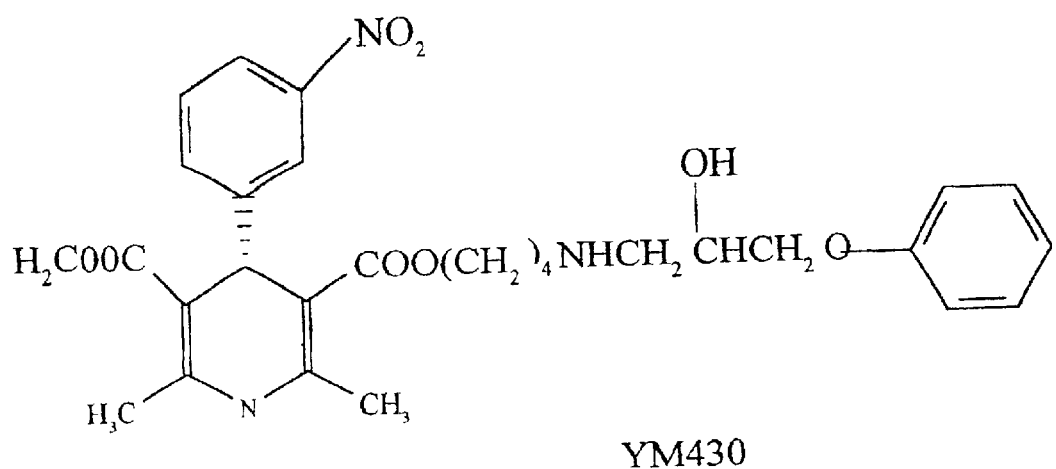
Figure 1:
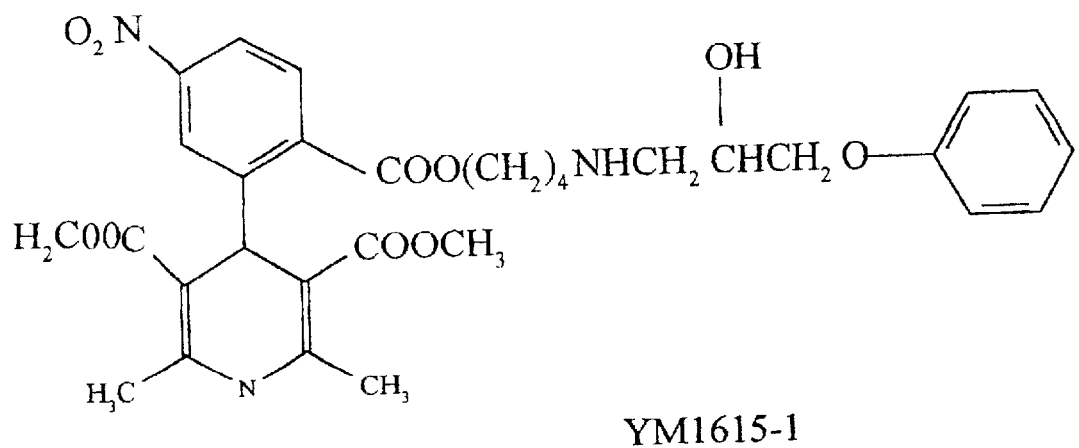

FIG. 1 illustrated the structures of compounds YM-16151-1 and YM 430.

Figure 2:
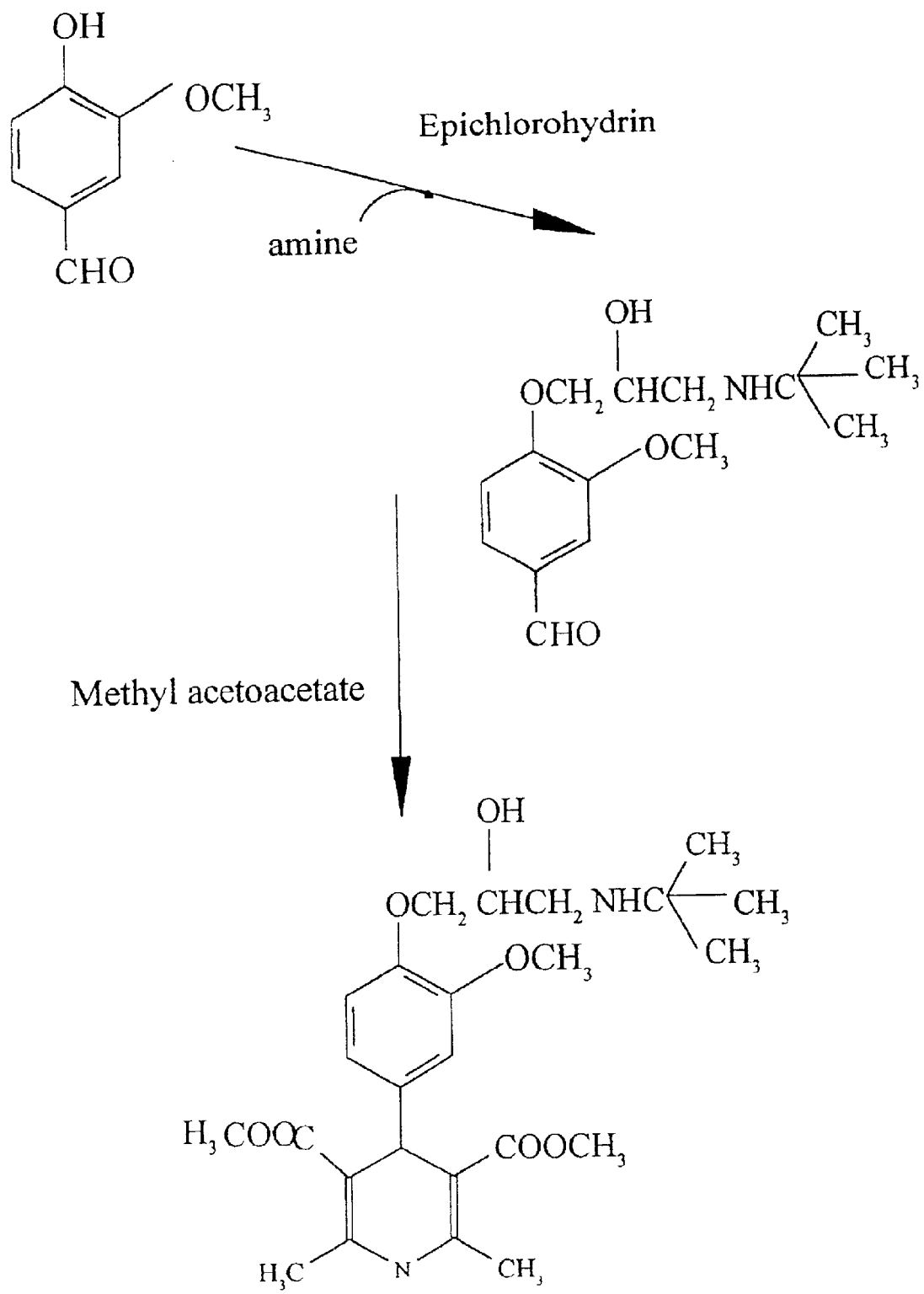

FIG. 2 illustrated the synthetic method of this invention compound.

Figure 3:
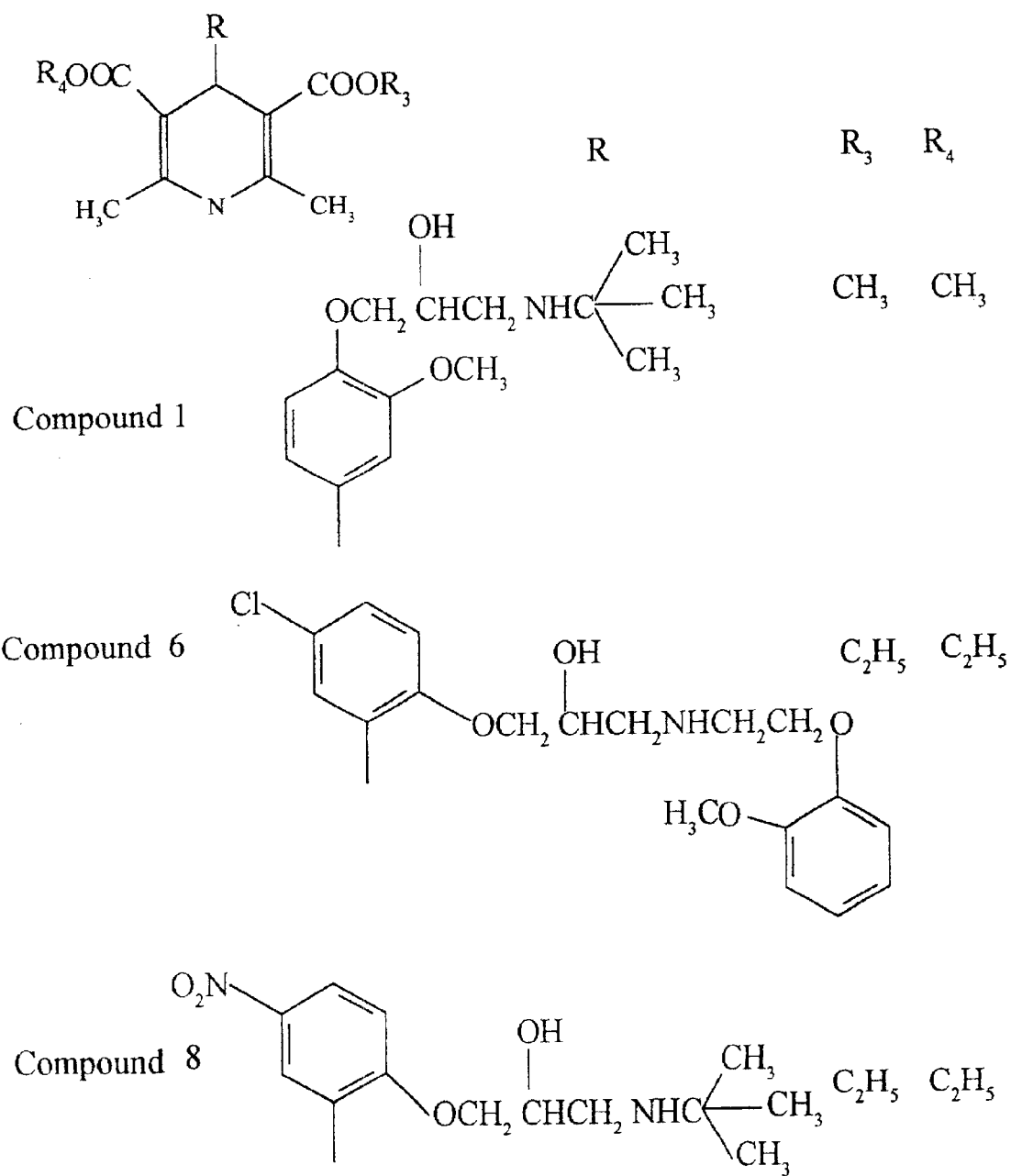

FIG. 3 illustrated the partial structures of this invention compound.

Figure 4A:
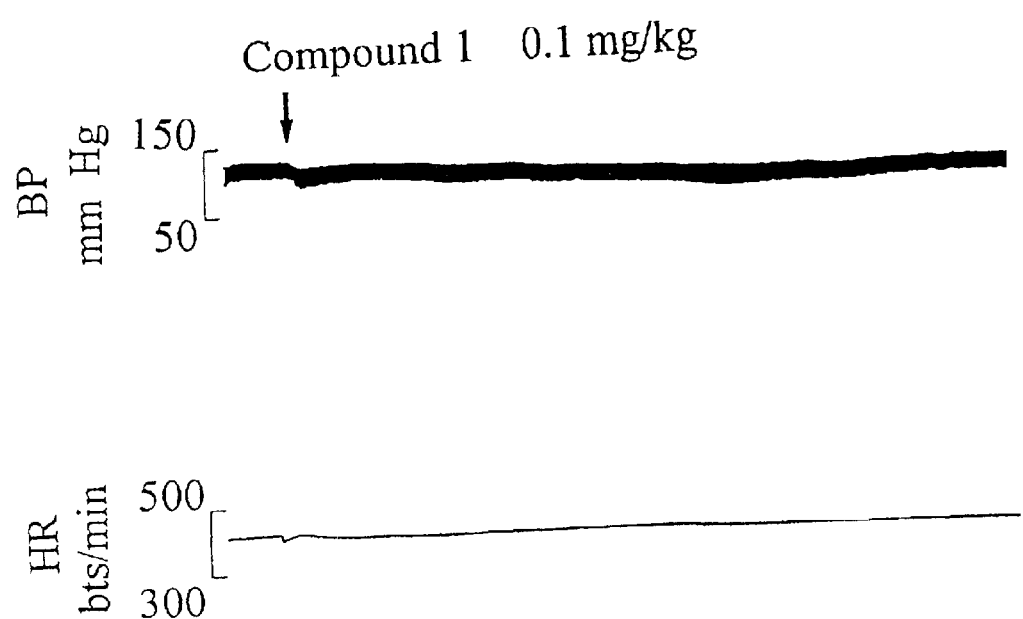

FIGS. 4a)-e) illustrated this invention compound on heart rate and hypertensive responses.

Figure 4B:
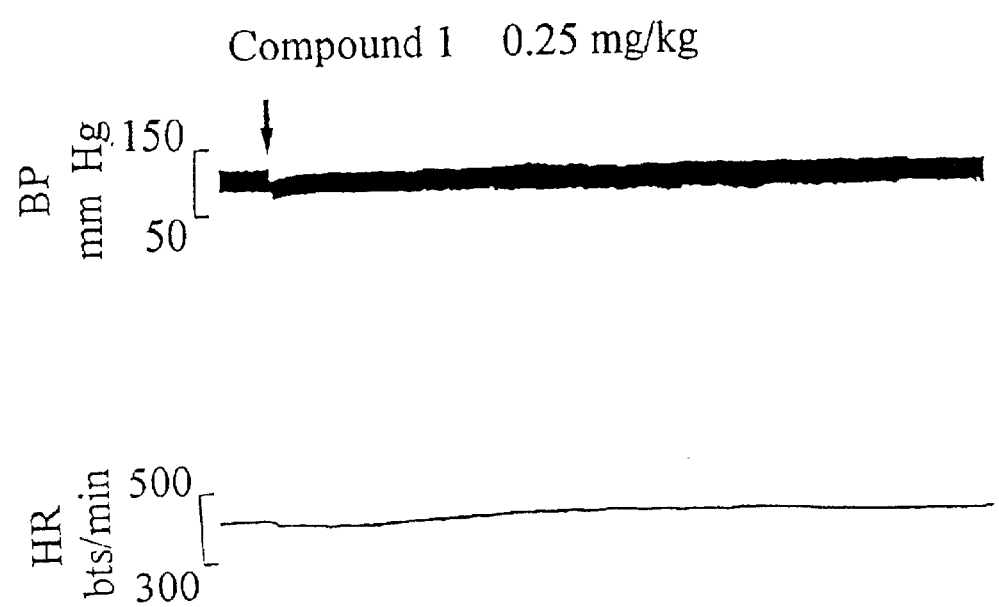
Figure 4C:
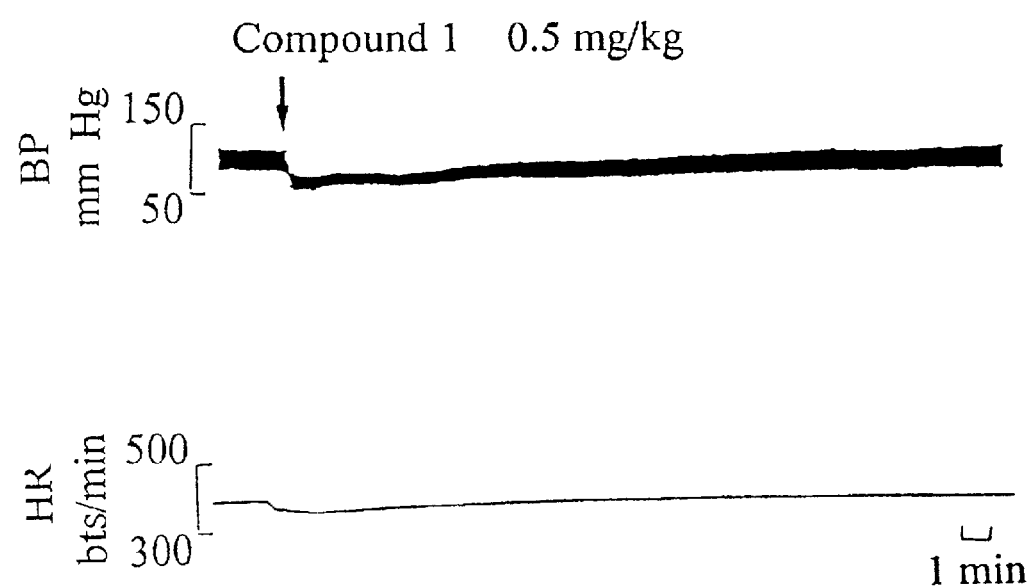
Figure 4D:
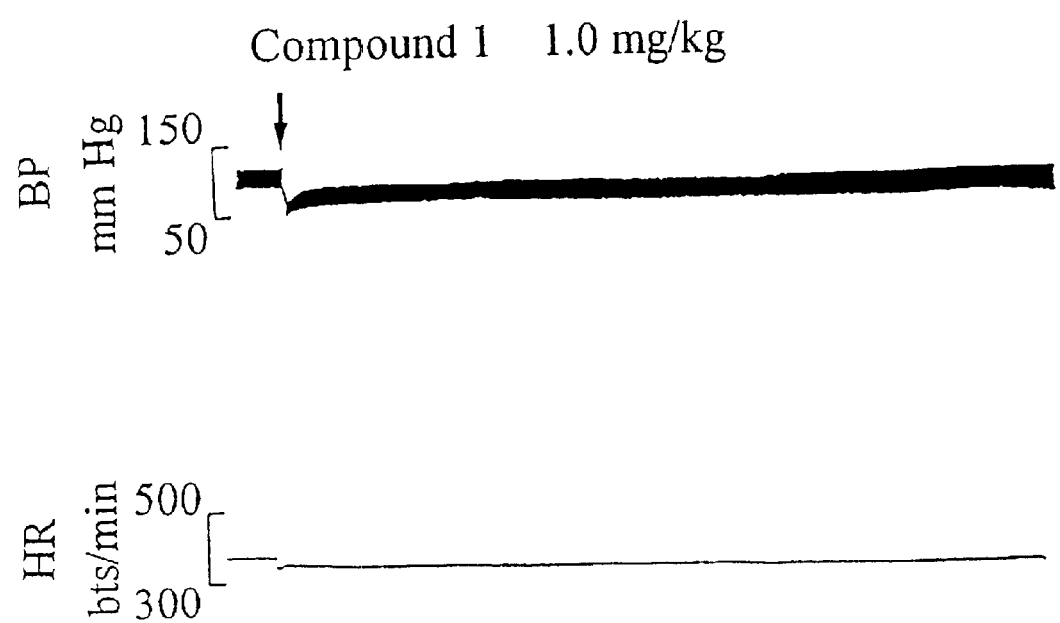
Figure 4E:
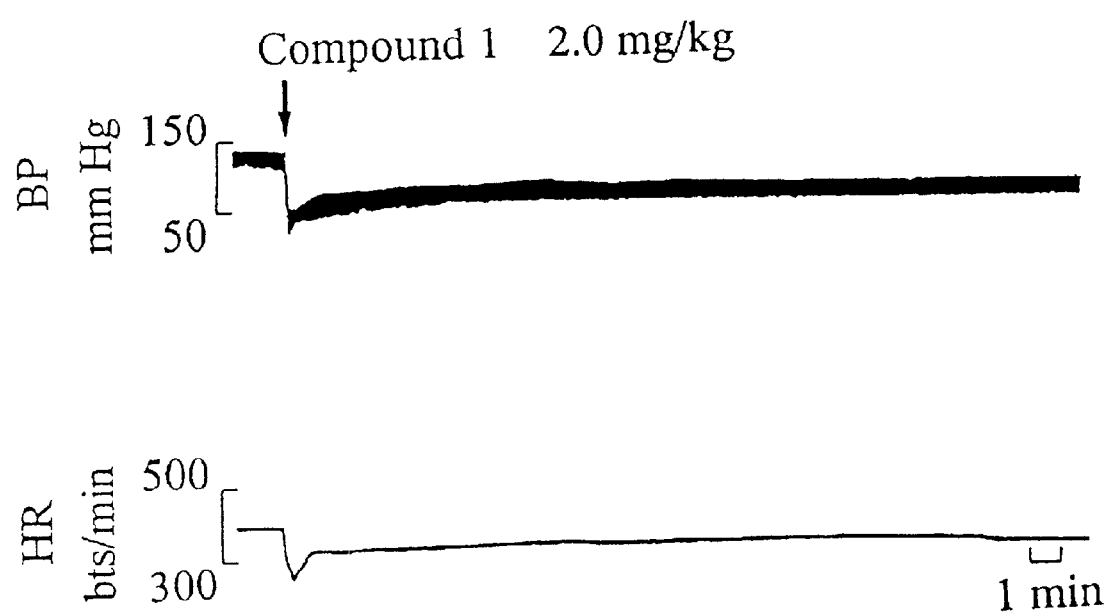

FIG. 4a) 0.1 mg/kg compound 1
FIG. 4b) 0.25 mg/kg compound 1
FIG. 4c) 0.5 mg/kg compound 1
FIG. 4d) 1.0 mg/kg compound 1
FIG. 4e) 2.0 mg/kg compound 1

Figure 5A:
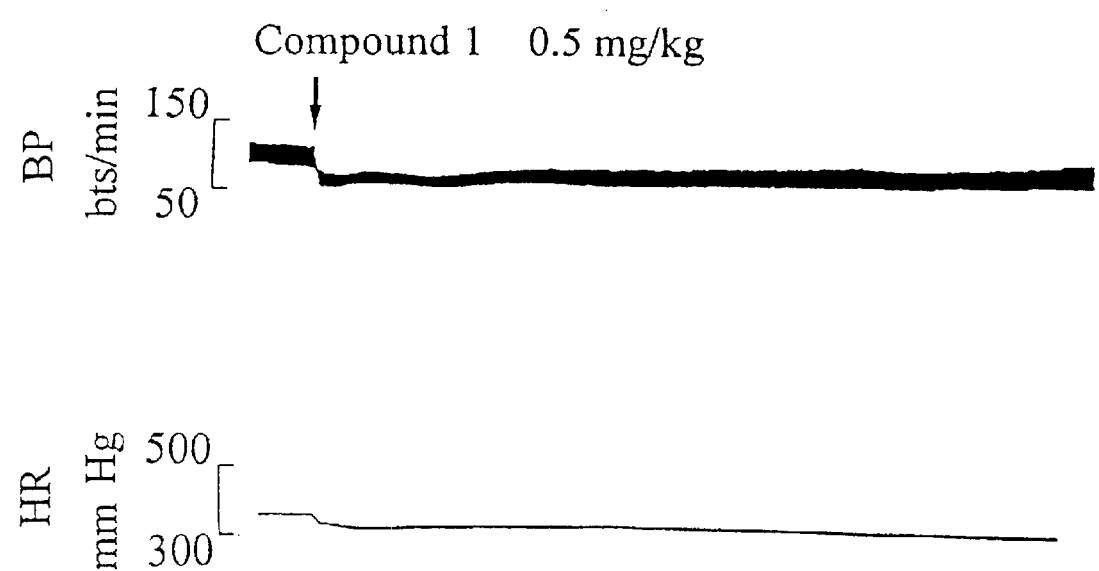

FIGS. 5a)-b)illustrated heart rate and hypertensive responses.

Figure 5B:
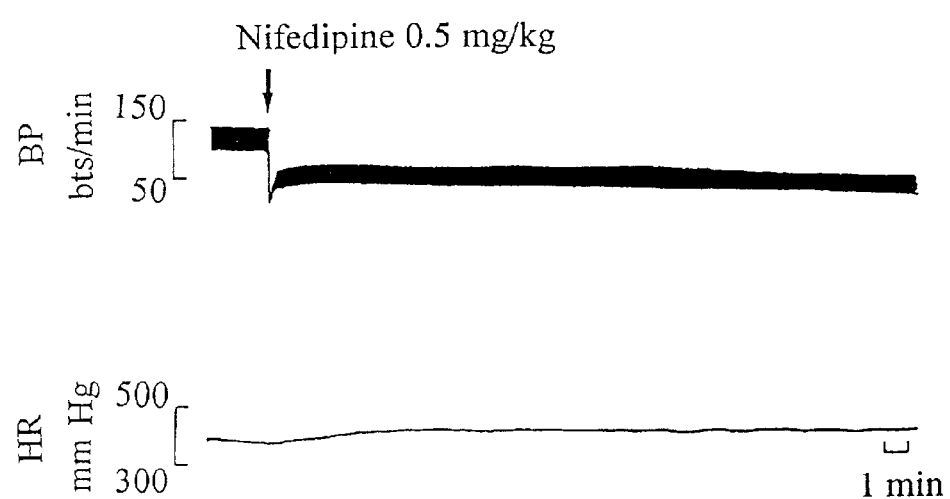

FIG. 5a) 0.5 mg/kg compound 1
FIG. 5b) 0. 5 mg/kg nifedipine

Figure 6:
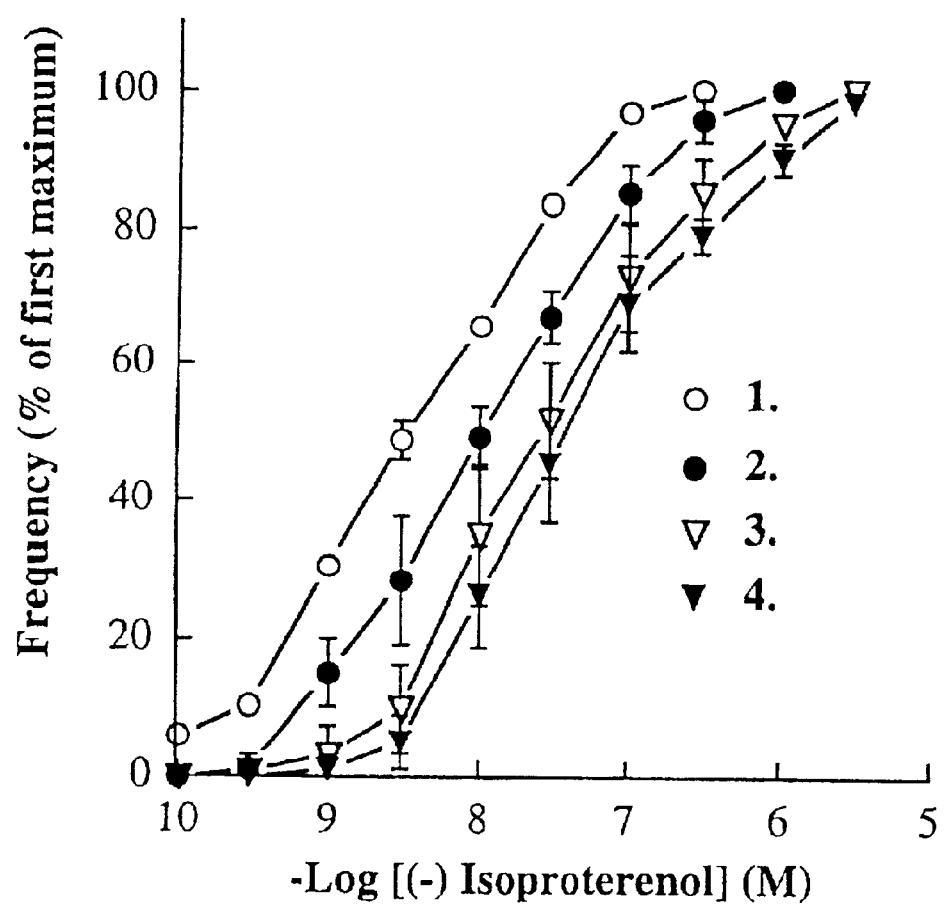

FIG. 6 illustrated a competitive blocking agent L-isoproterenol on increasing heart rate.

1 . . . control
2 . . . $10^{-7}$ M compound 1
3 . . . $10^{-6}$ M compound 1
4 . . . $10^{-5}$ M compound 1

Figure 7:
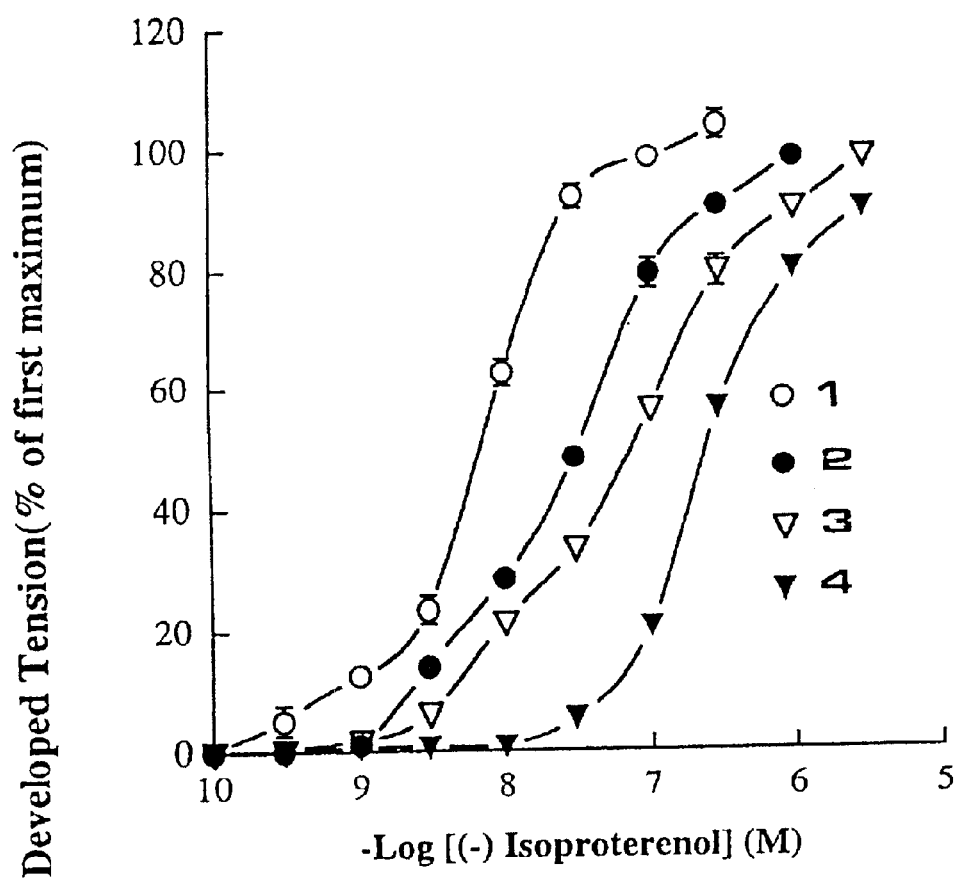

FIG. 7 illustrated a competitive blocking agent L-isoproterenol on increasing heart rate.

1 . . . control
2 . . . $10^{-7}$ M compound 1
3 . . . $10^{-6}$ M compound 1
4 . . . $10^{-5}$ M compound 1

Figure 8:
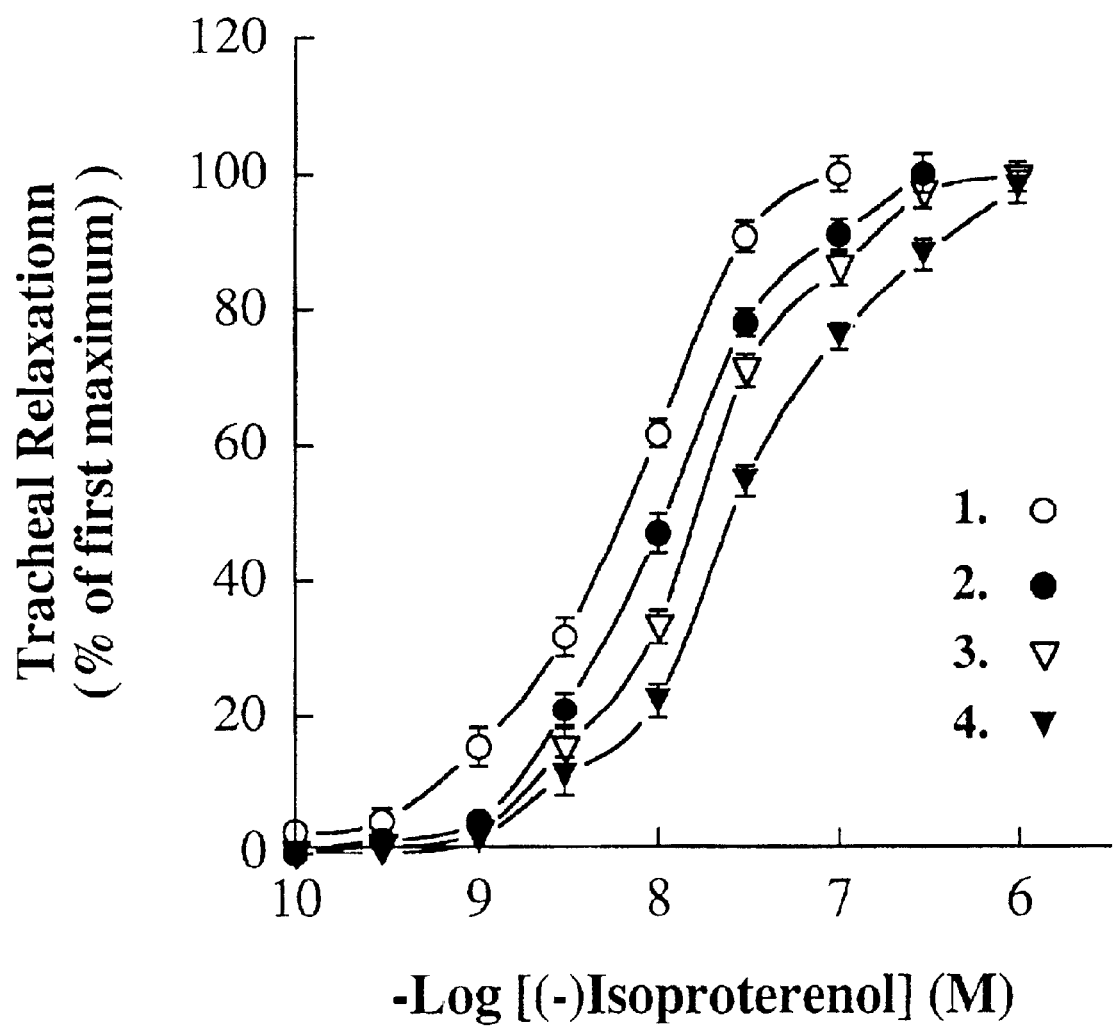

FIG. 8 illustrated a competitive blocking agent L-isoproterenol on bronchoconstrictive effect.
1 . . . control
2 . . . $10^{-7}$ M compound 1
3 . . . $10^{-6}$ M compound 1
4 . . . $10^{-5}$ M compound 1

Figure 9:
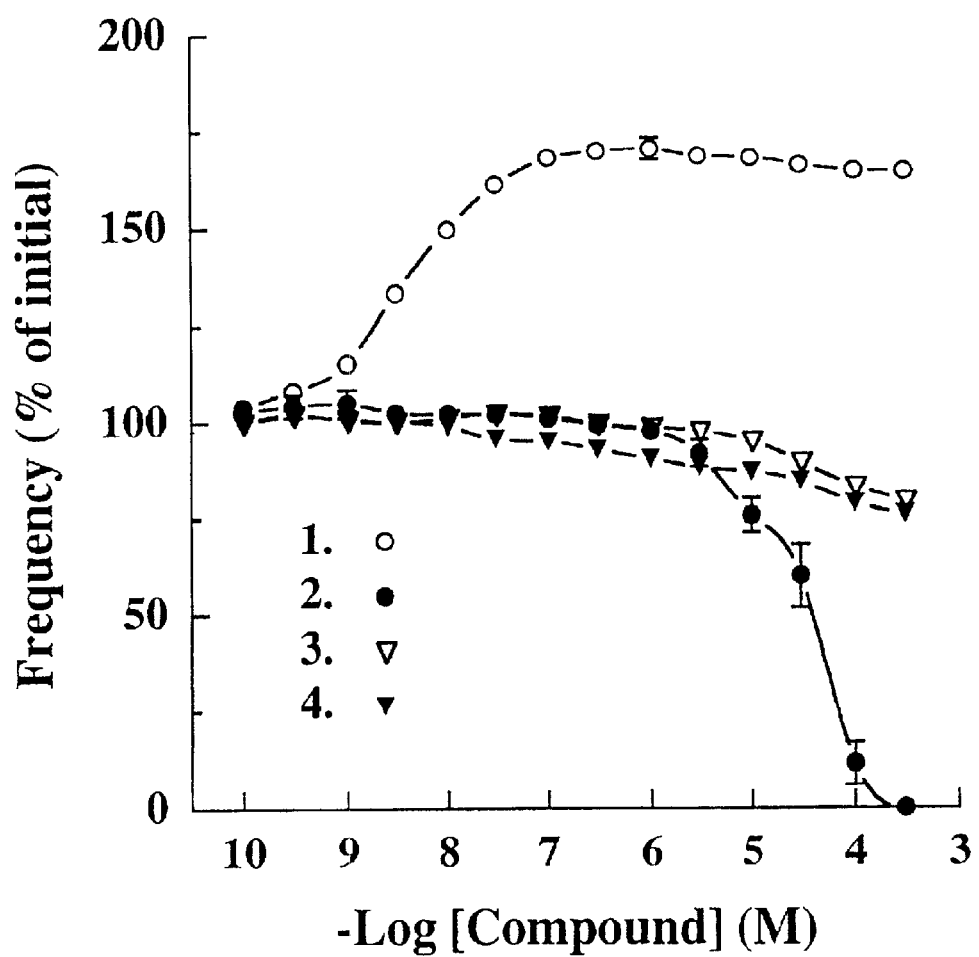

FIG. 9 illustrated L-isoproterenol on right atrial rate
1 . . . L-isoproterenol
2 . . . PROPRANOLOL
3 . . . VANIDILOL
4 . . . compound 1

Figure 10:
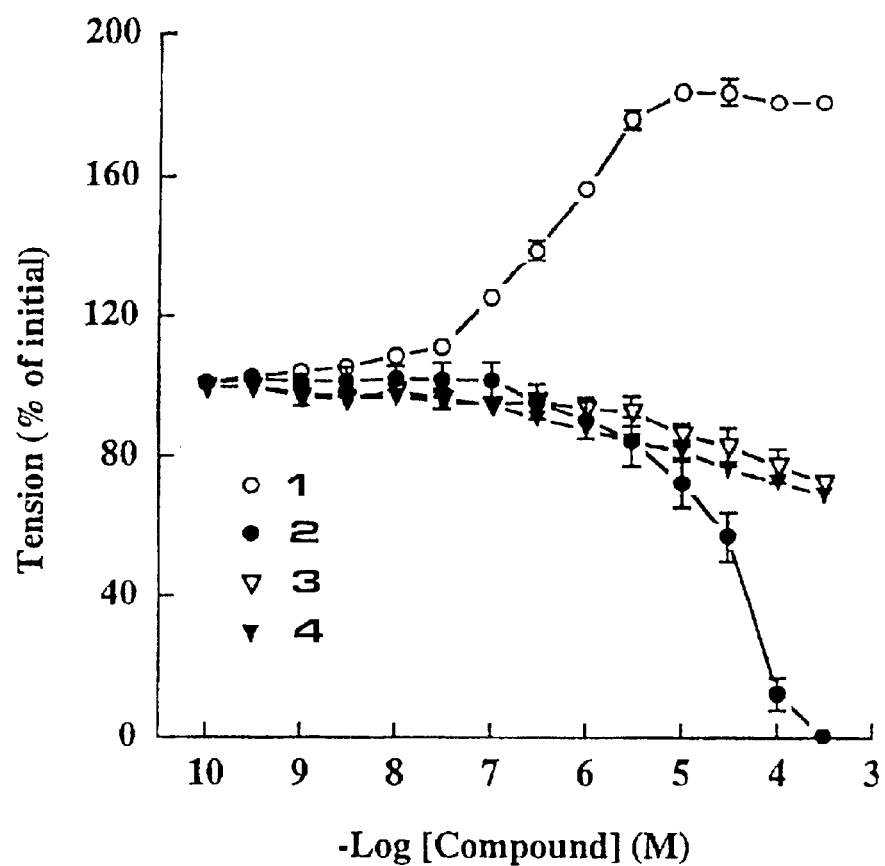

FIG. 10 illustrated L-isoproterenol on left atrial systole tension
1 . . . L-isoproterenol
2 . . . PROPRANOLOL
3 . . . VANIDILOL
4 . . . compound 1

Figure 11:
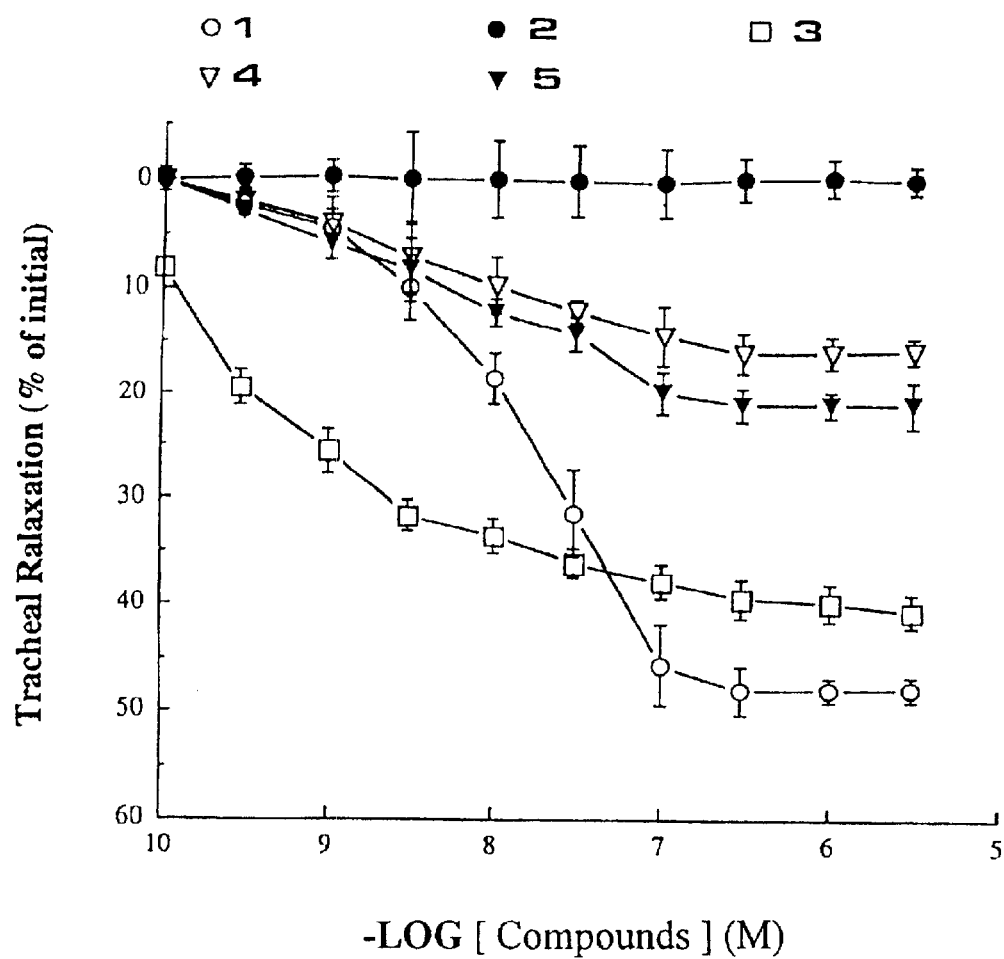

FIG. 11 illustrated the effect of this invention compound on tracheal relaxant.
1 . . . L-isoproterenol
2 . . . PROPRANOLOL
3 . . . NIFEDIPINE
4 . . . VANIDILOL
5 . . . compound 1

Figure 12:
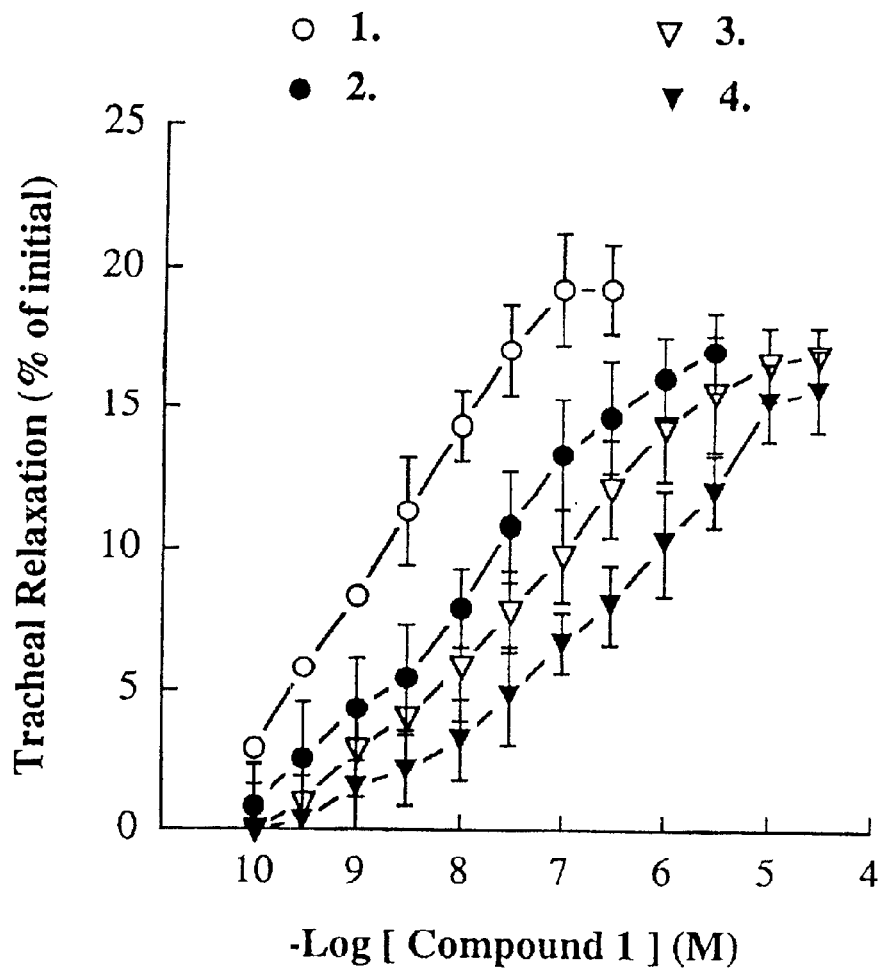

FIG. 12 illustrated the effect of this invention compound on tracheal relaxant.
1 . . . control
2 . . . $10^{-10}$ M ICI 118, 551
3 . . . $10^{-9}$ M ICI 118 551
4 . . . $10^{-8}$ M ICI 118, 551

Figure 13:
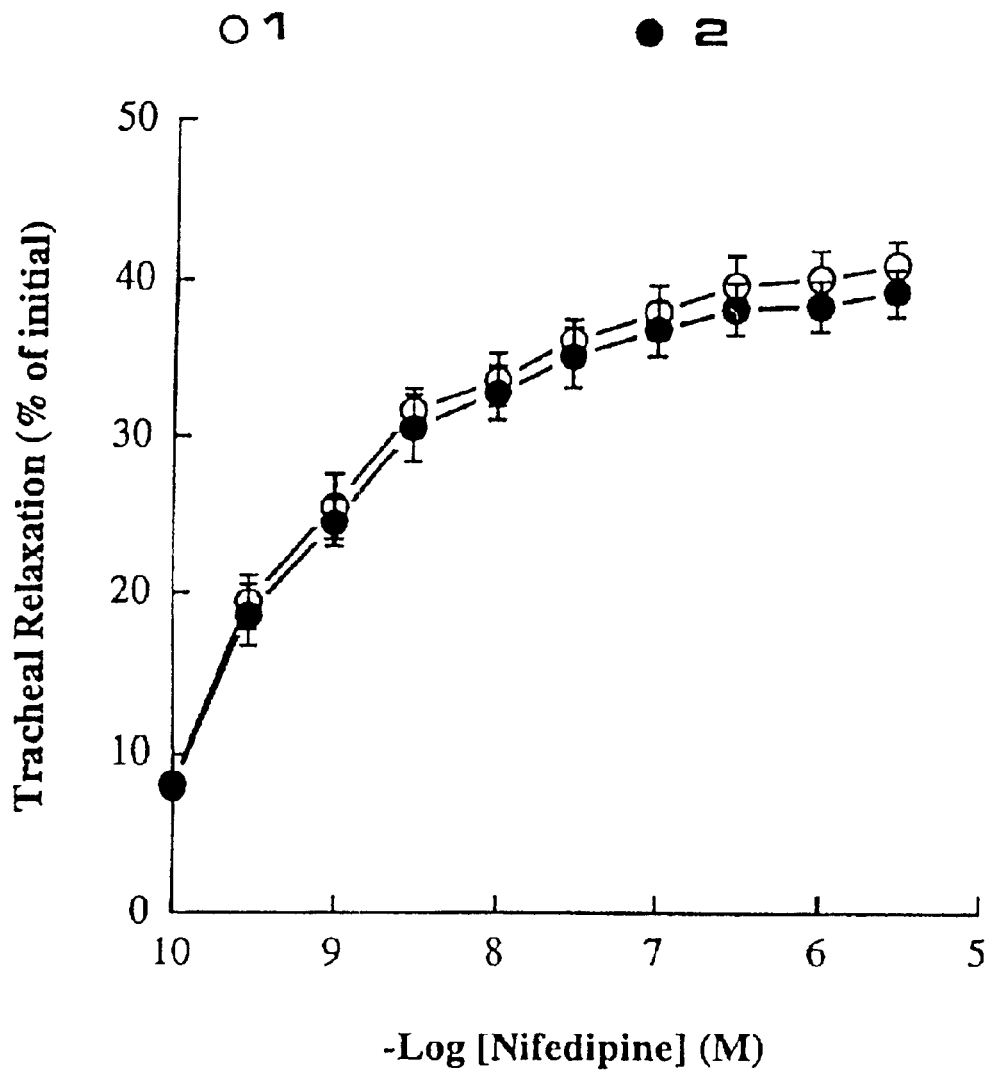

FIG. 13 illustrated the effect of this invention compound on tracheal relaxant.
1 . . . control
2 . . . $10^{-8}$ M ICI 118, 551

Figure 14A:
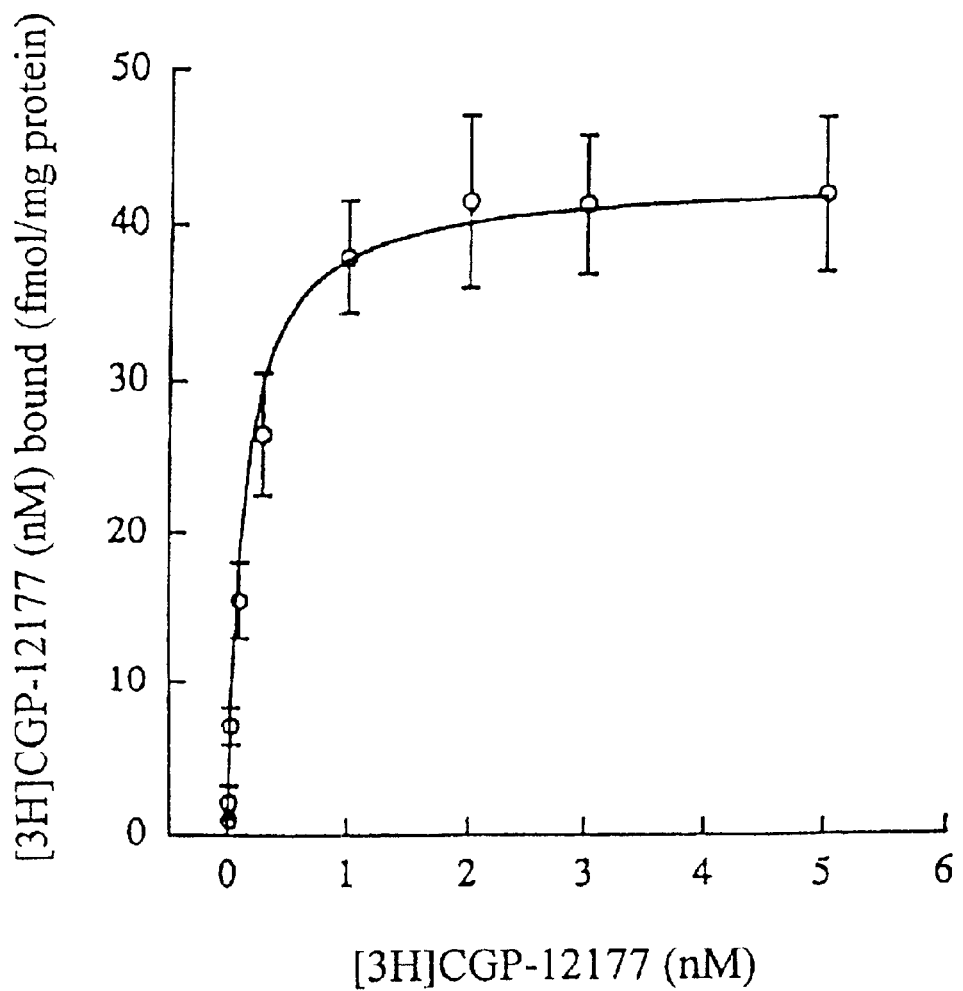
Figure 14B:
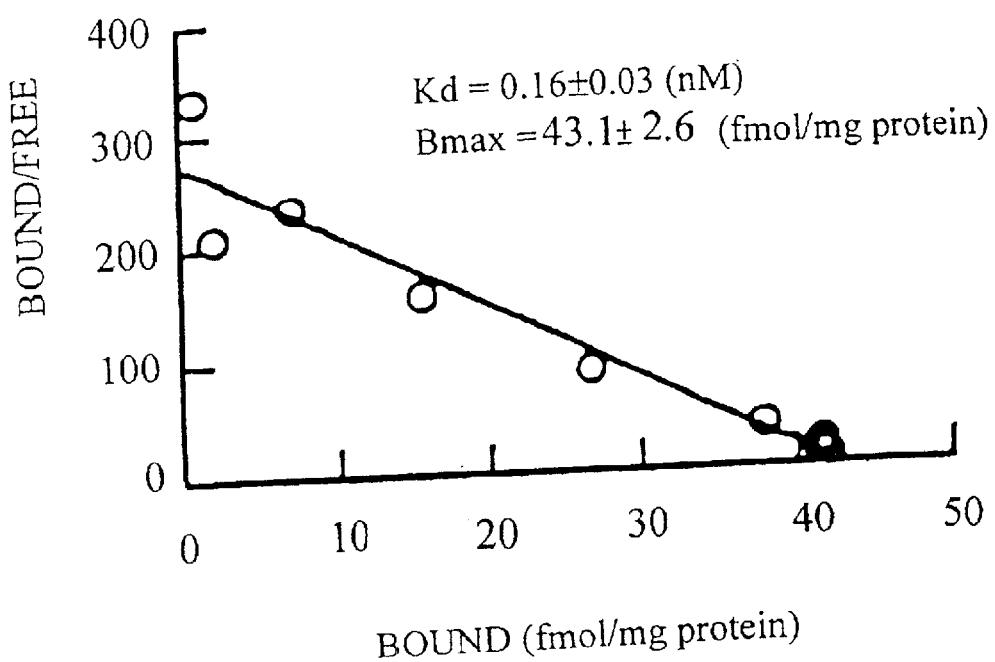
Figure 15:
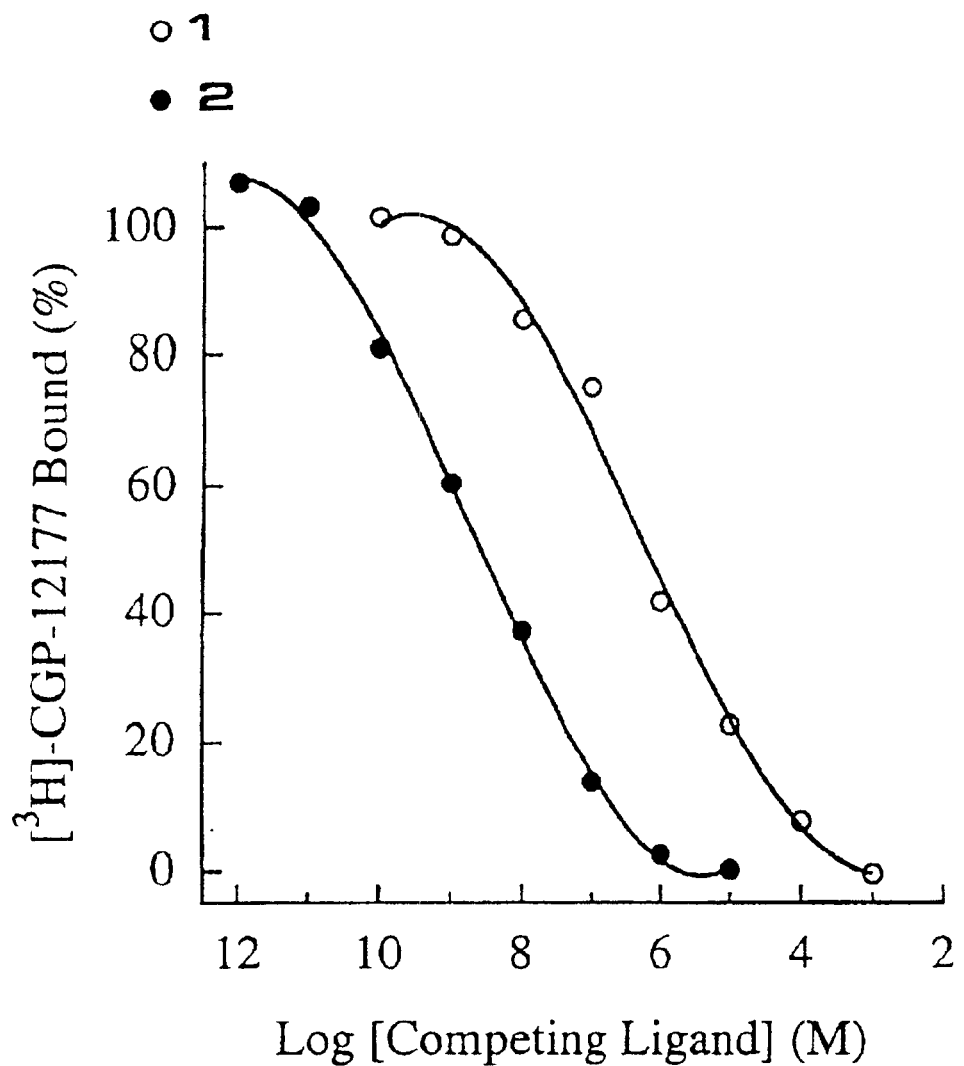
Figure 16A:
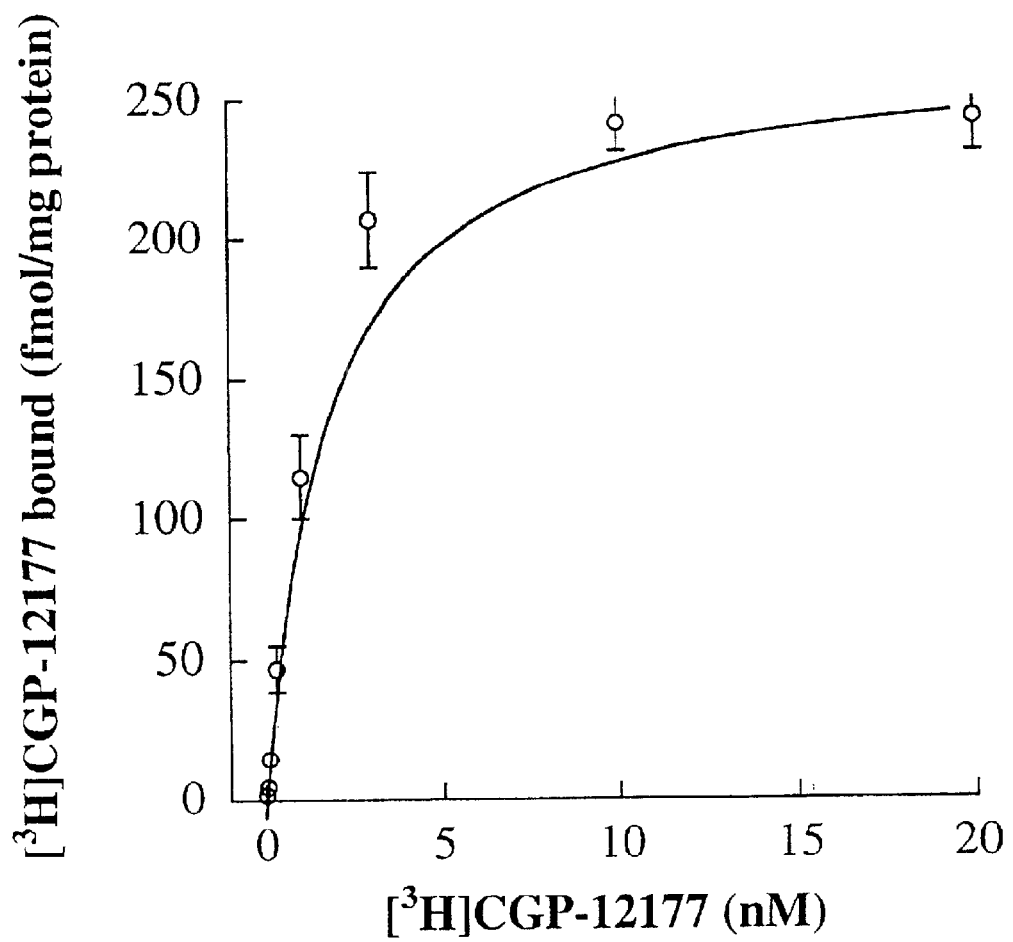
Figure 16B:
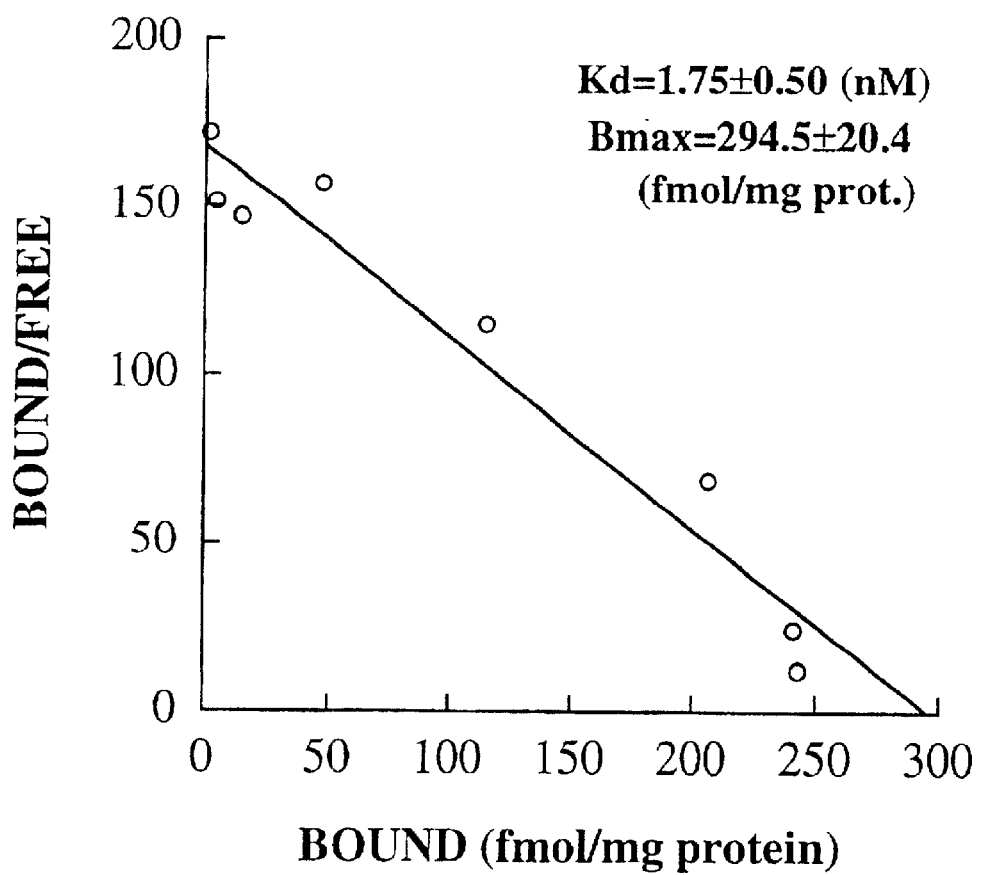
Figure 17:
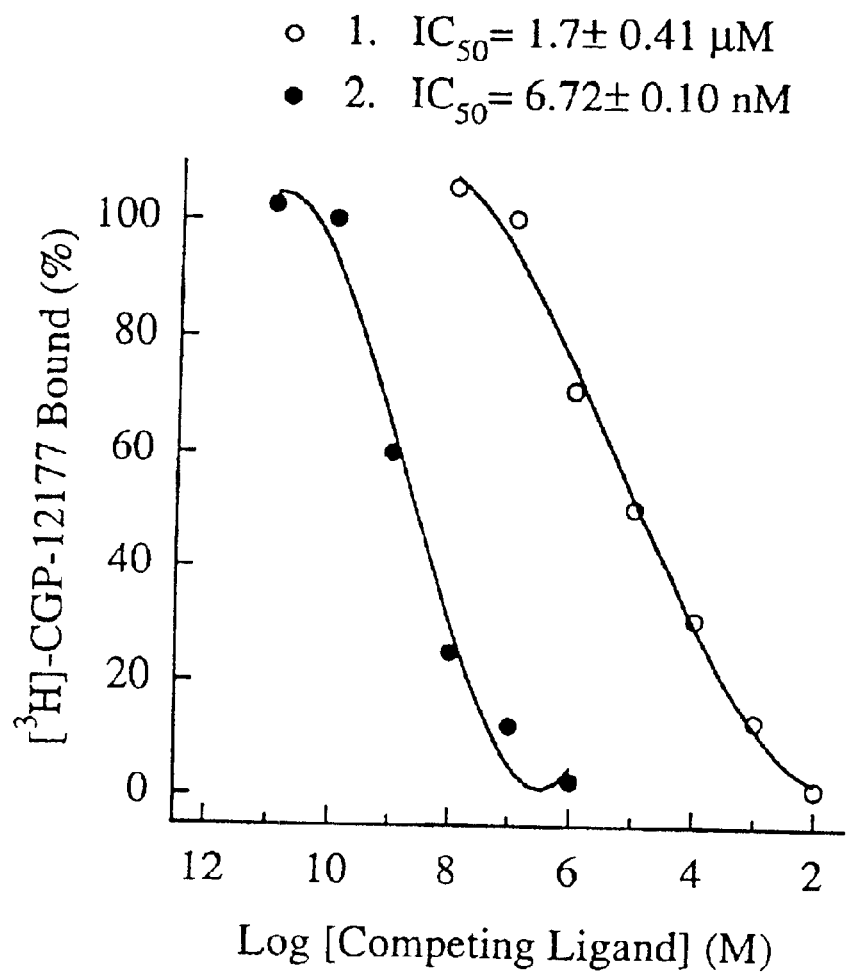
Figure 18A:
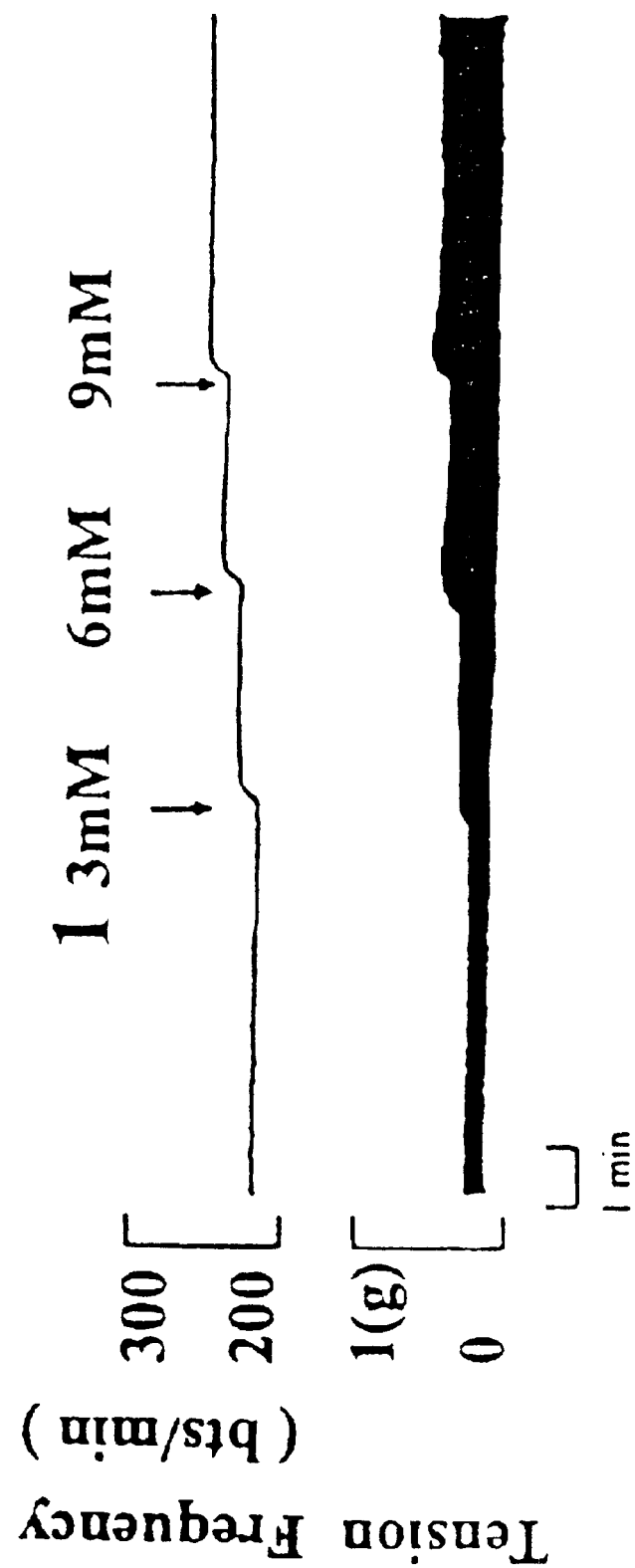
Figure 18B:
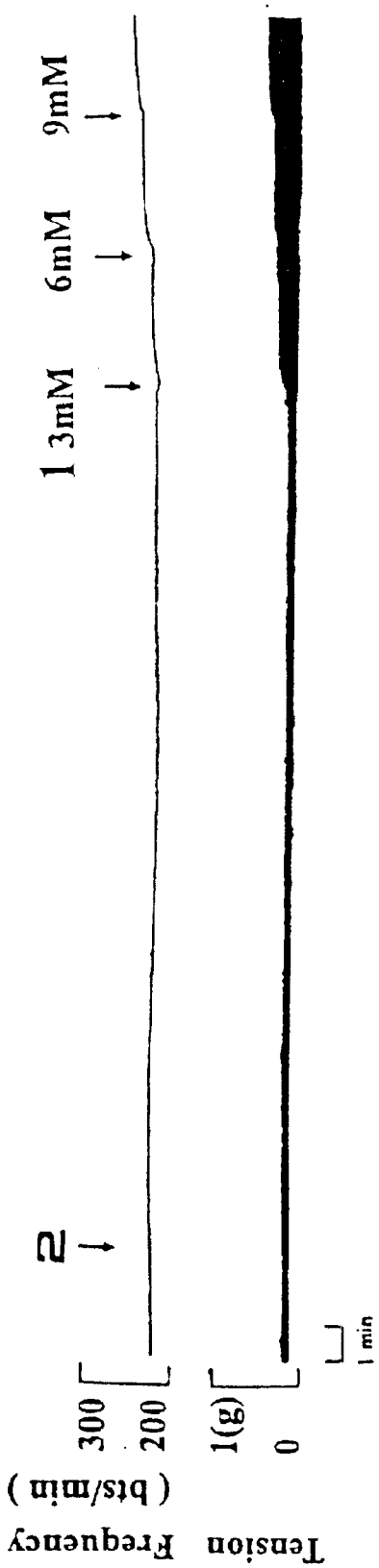
Figure 18C:
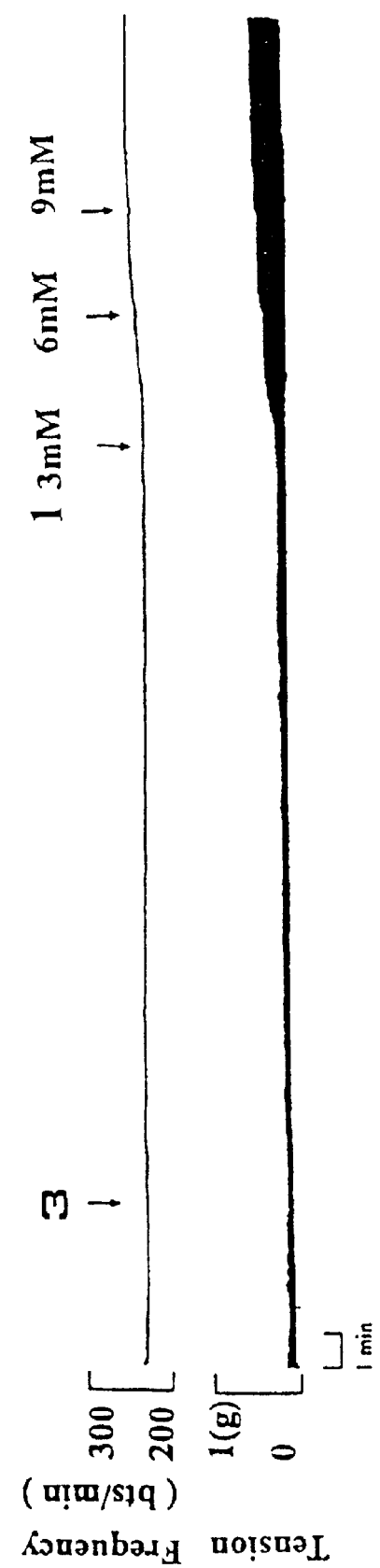
Figure 18D:
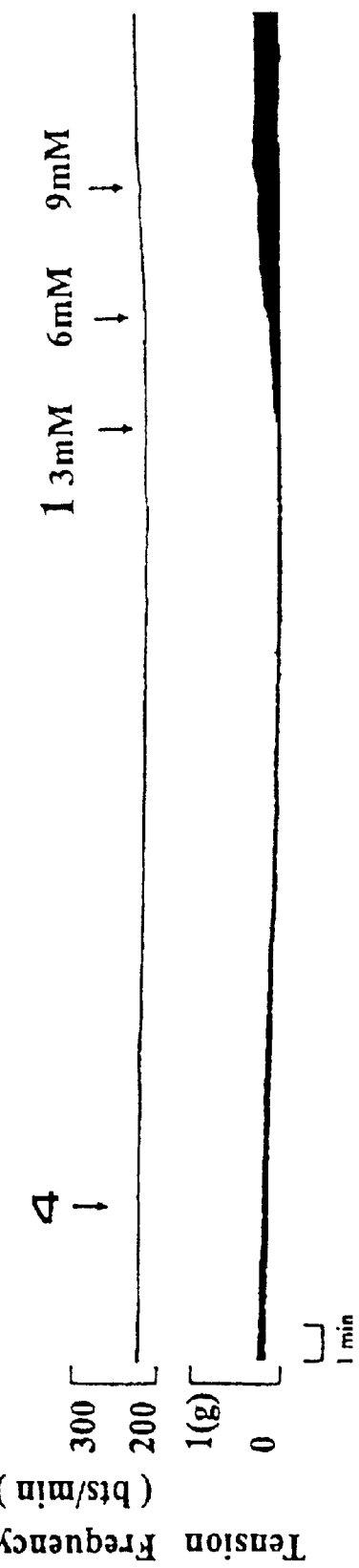

FIGS. 14 a)-b) illustrated this invention compound on receptor binding.
FIG. 14 a) [$^3$H]CGP-12177 bound
FIG. 14 b) protein bound FIG. 15 illustrated competitive curve of β-adrenoceptor blocking agent
1 . . . compound 1
2 . . . PROPRANOLOL FIG. 16 a)-b) illustrated this invention compound on combined receptors.
FIG. 16 a) [$^3$H]CGP-12177 bound
FIG. 16 b) protein bound FIG. 17 illustrated competitive curve of, β-adrenoceptor blocking agent
1 . . . compound 1
2 . . . PROPRANOLOL FIG. 18 illustrated the effect of this invention compound on atrial rate.
a . . . control
b . . . $10^{-7}$ M compound 1
c . . . $10^{-6}$ M compound 1
d . . . $10^{-5}$ M compound 1

Figure 19:
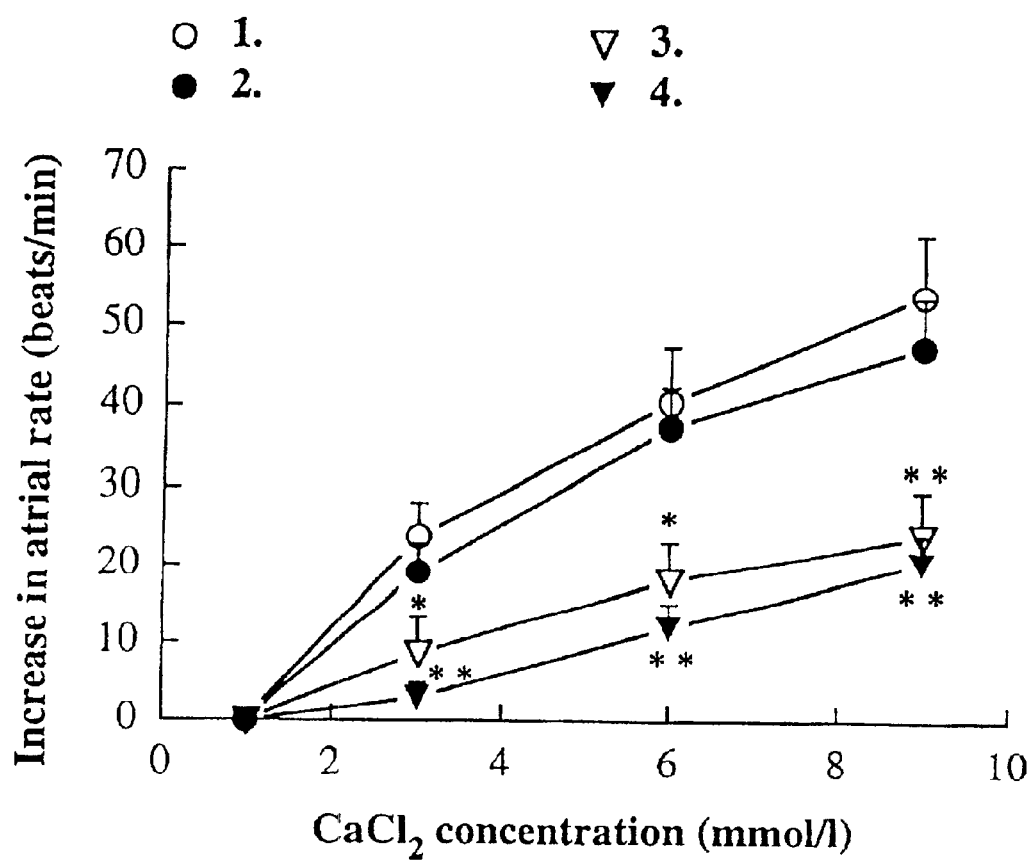
Figure 20A:
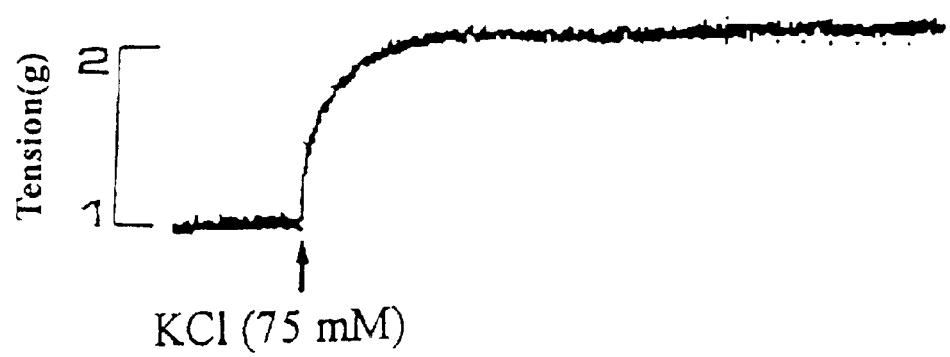
Figure 20B:
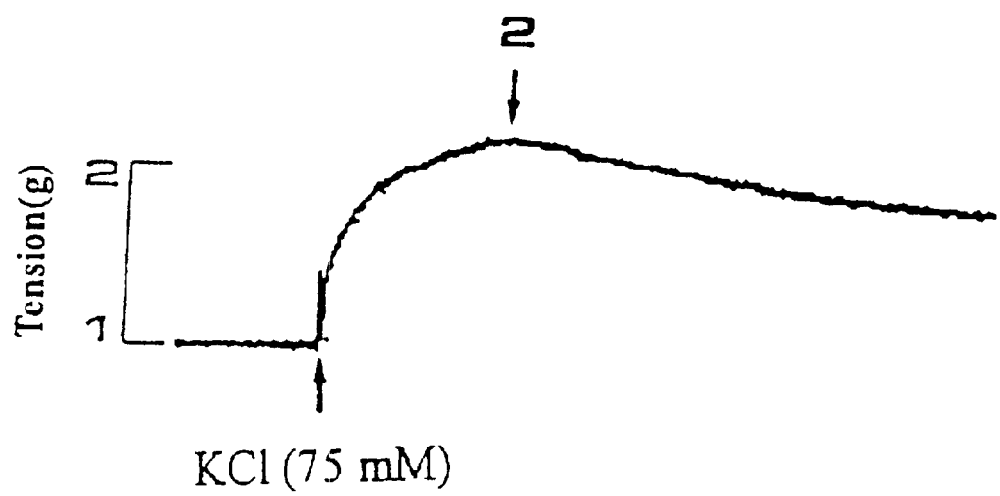
Figure 20C:
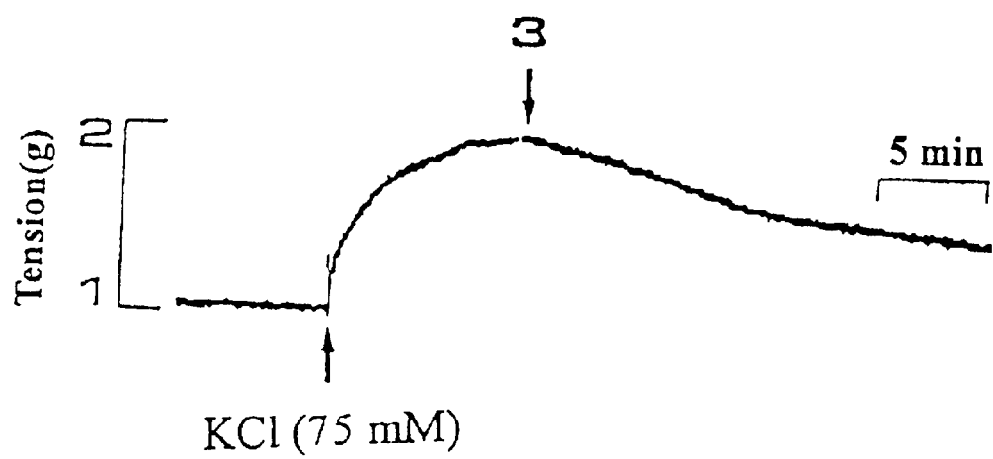
Figure 20D:
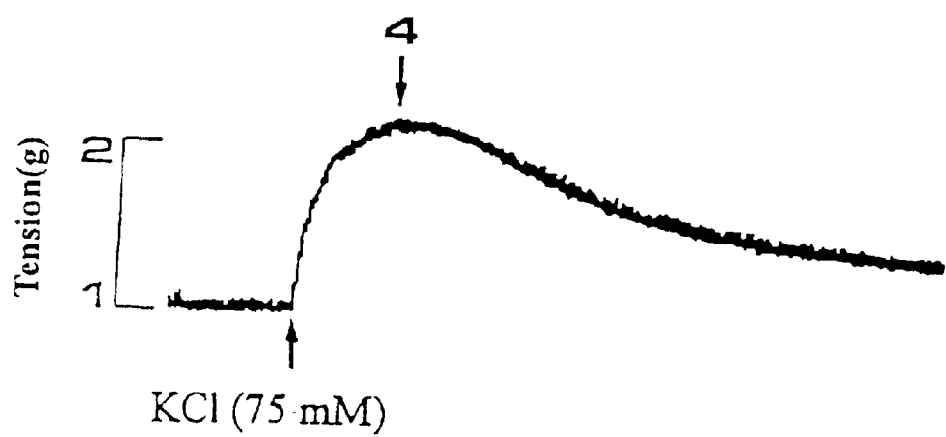
Figure 20E:
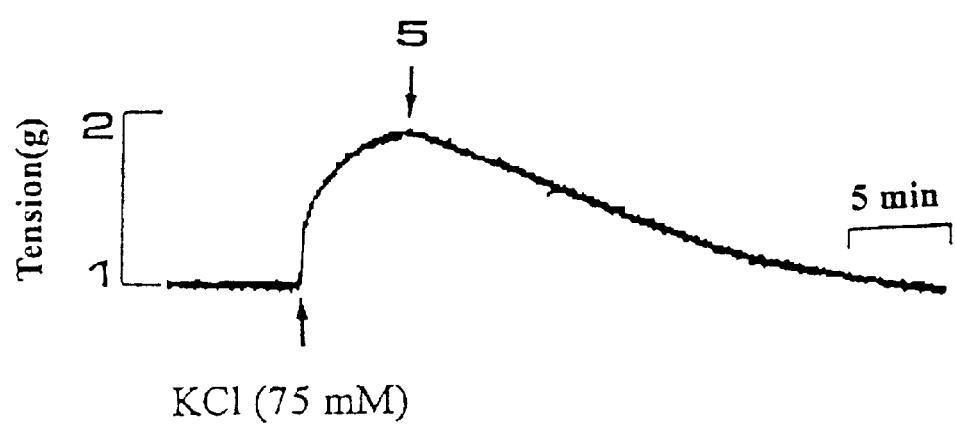
Figure 21A:
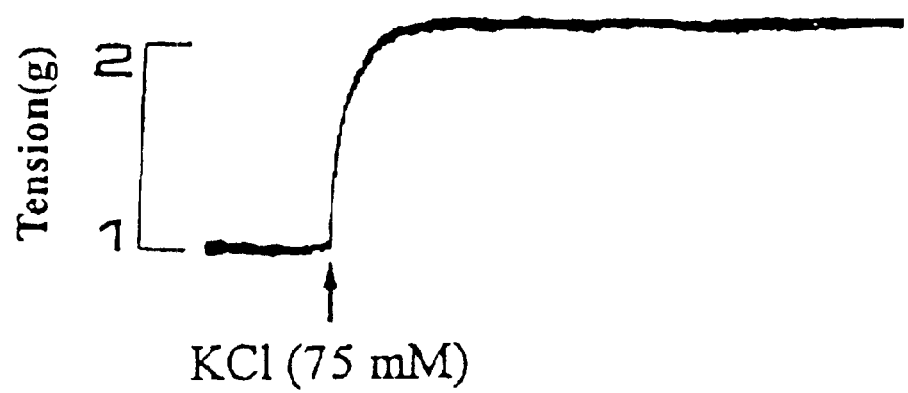
Figure 21B:
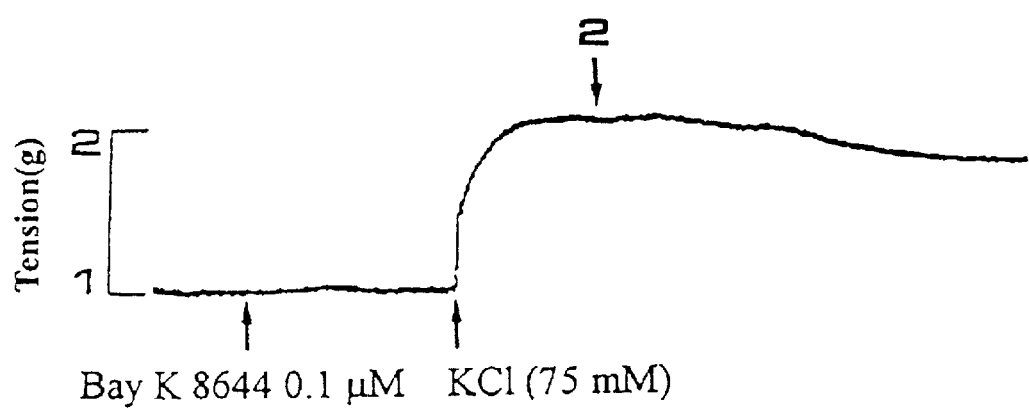
Figure 21C:
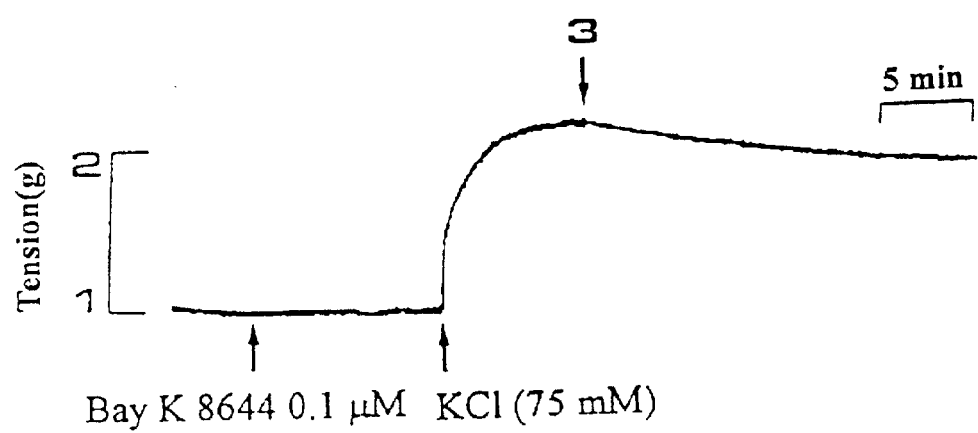
Figure 21D:
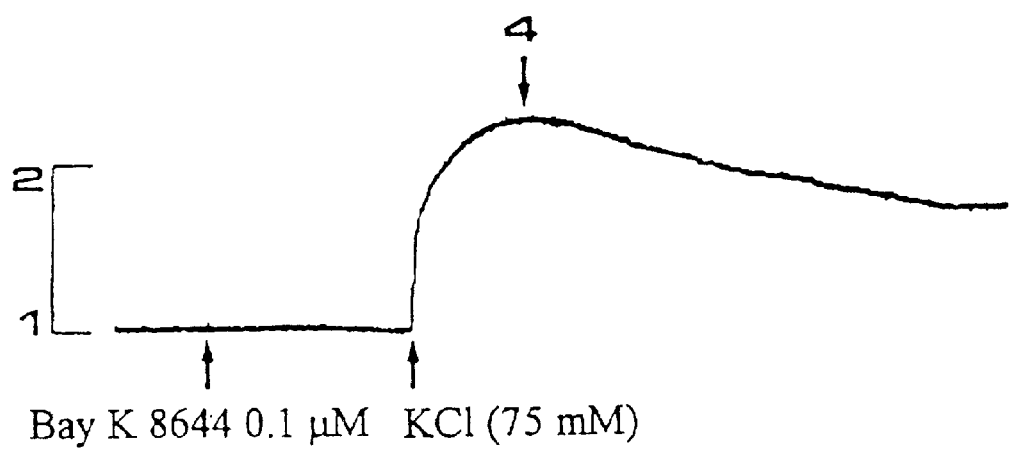
Figure 21E:
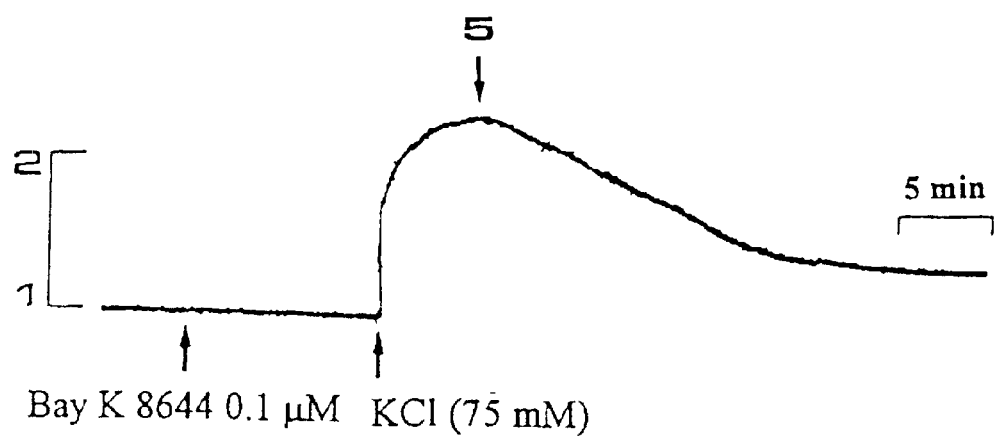

FIG. 19 illustrated the effect of this invention compound on atrial rate.
1 . . . control
2 . . . $10^{-7}$ M compound 1
3 . . . $10^{-6}$ M compound 1
4 . . . $10^{-5}$ M compound 1

FIG. 20 illustrated the effect of this invention compound on vasorelaxant.
a . . . control
b . . . $10^{-8}$ M compound 1
c . . . $10^{-7}$ M compound 1
d . . . $10^{-6}$ M compound 1
e . . . $10^{-5}$ M compound 1

FIG. 21 illustrated pre-treatment with Bay K 8644 will affect vasorelaxant effects.
a . . . control
b . . . $10^{-8}$ M compound 1
c . . . $10^{-7}$ M compound 1
d . . . $10^{-6}$ M compound 1
e . . . $10^{-5}$ M compound 1

Figure 22:
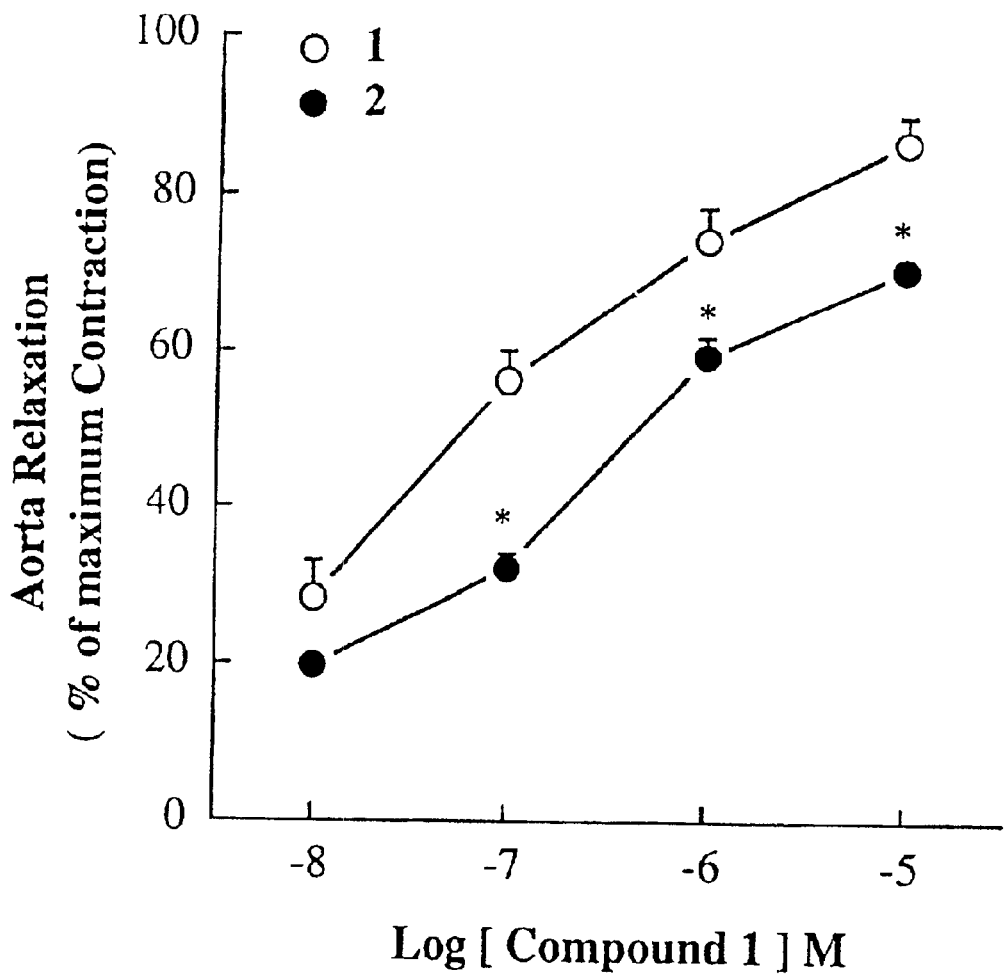

FIG. 22 illustrated pre-treatment with Bay K 8644 will affect to vasorelaxant effects.
1 . . . control
2 . . . Treatment before Bay K 8644

Figure 23A:
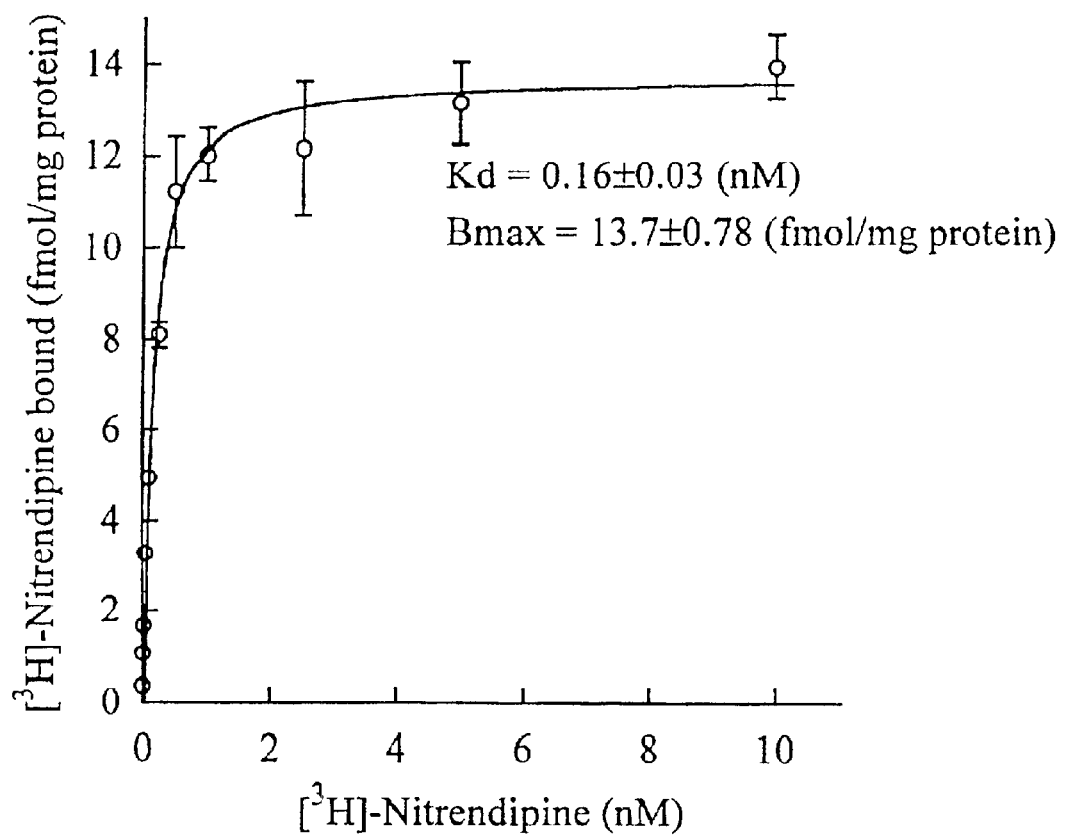
Figure 23B:
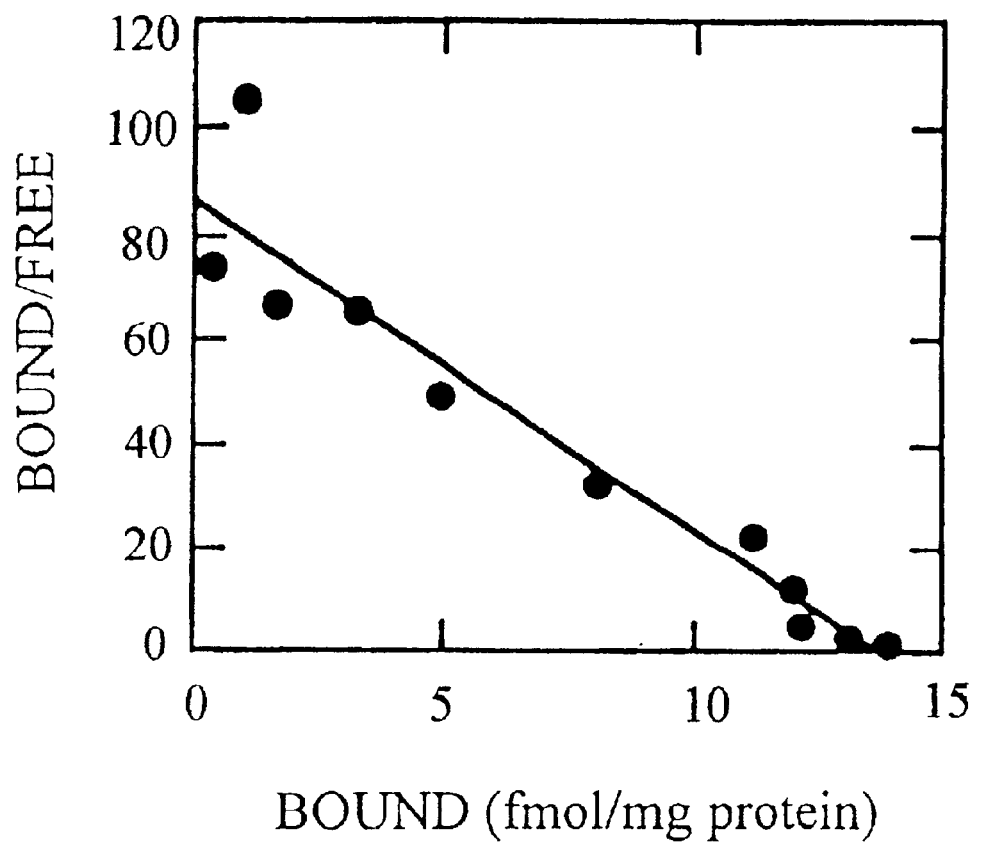
Figure 24:
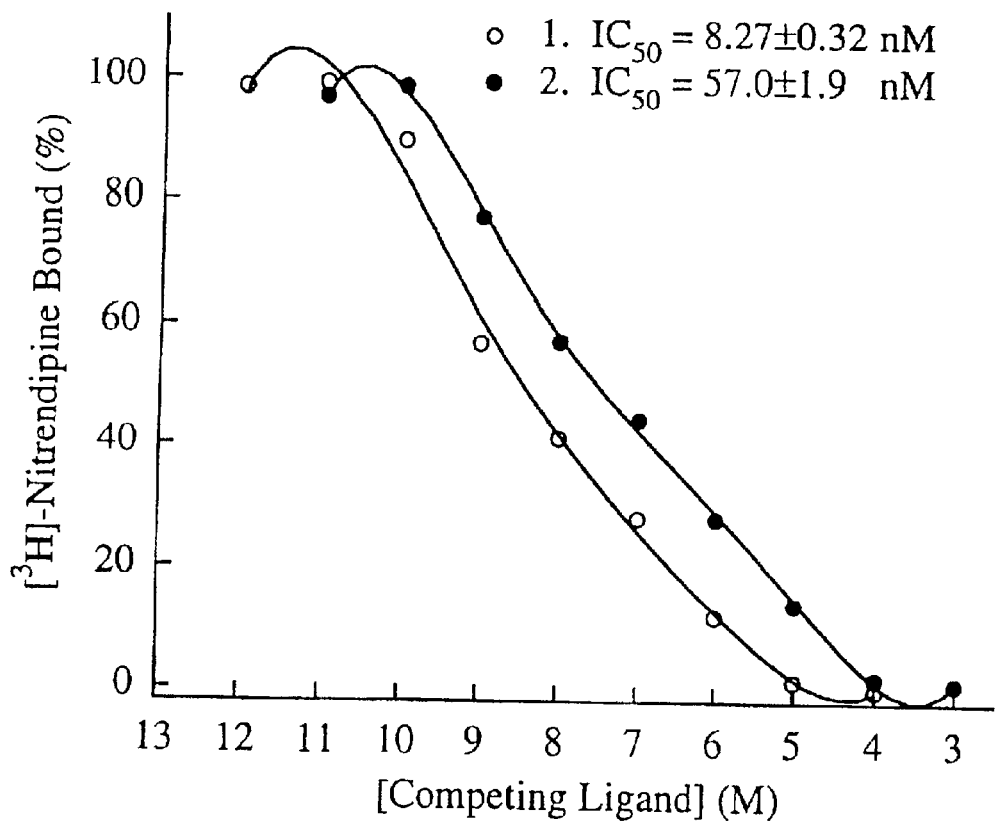

FIGS. 23 a)-b) illustrated [$^3$H]nitrendipine on receptor binding.
FIG. 23 a) [$^3$H]nitrendipine receptor bound
FIG. 23 b) protein bound FIG. 24 illustrated competitive curve of calcium ion entry blocking agent.
1 . . . nifedipine
2 . . . compound 1

Figure 25:
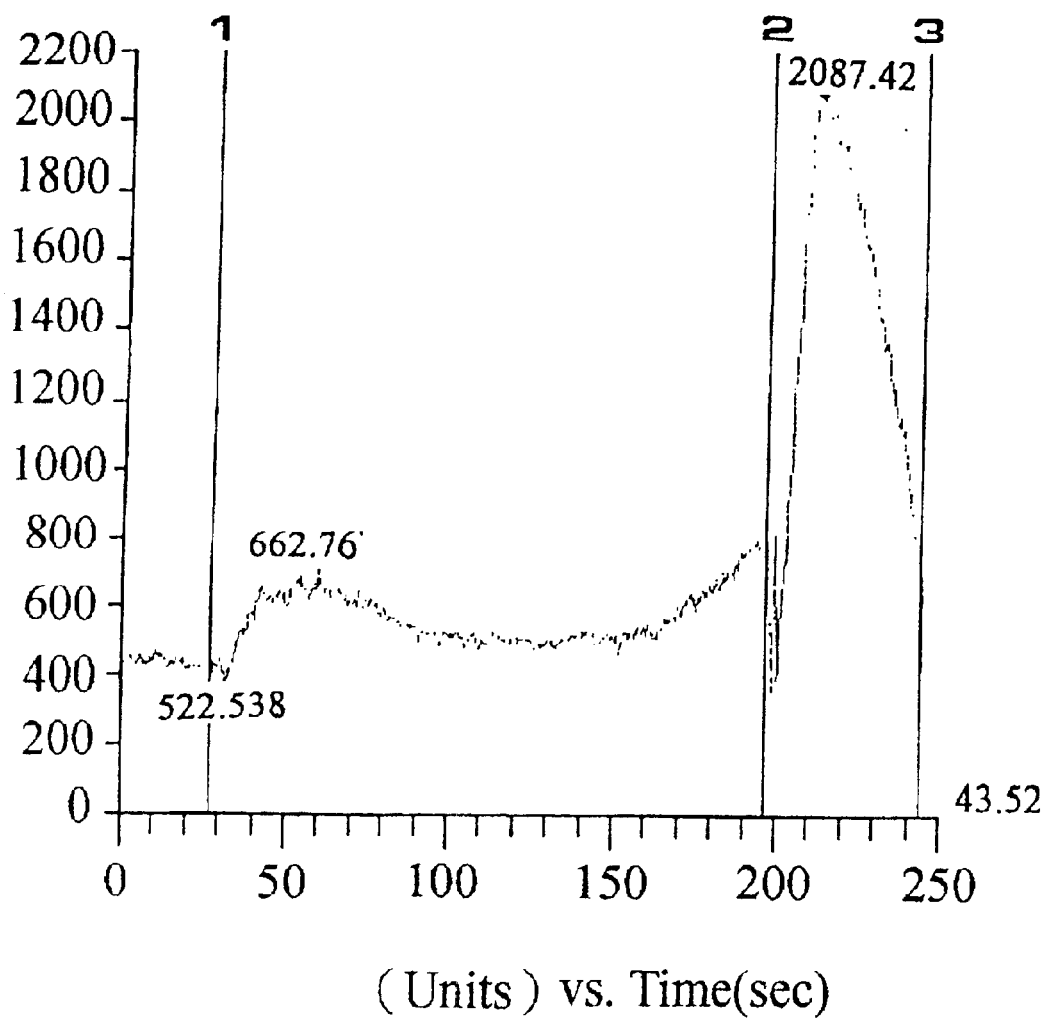
Figure 26:
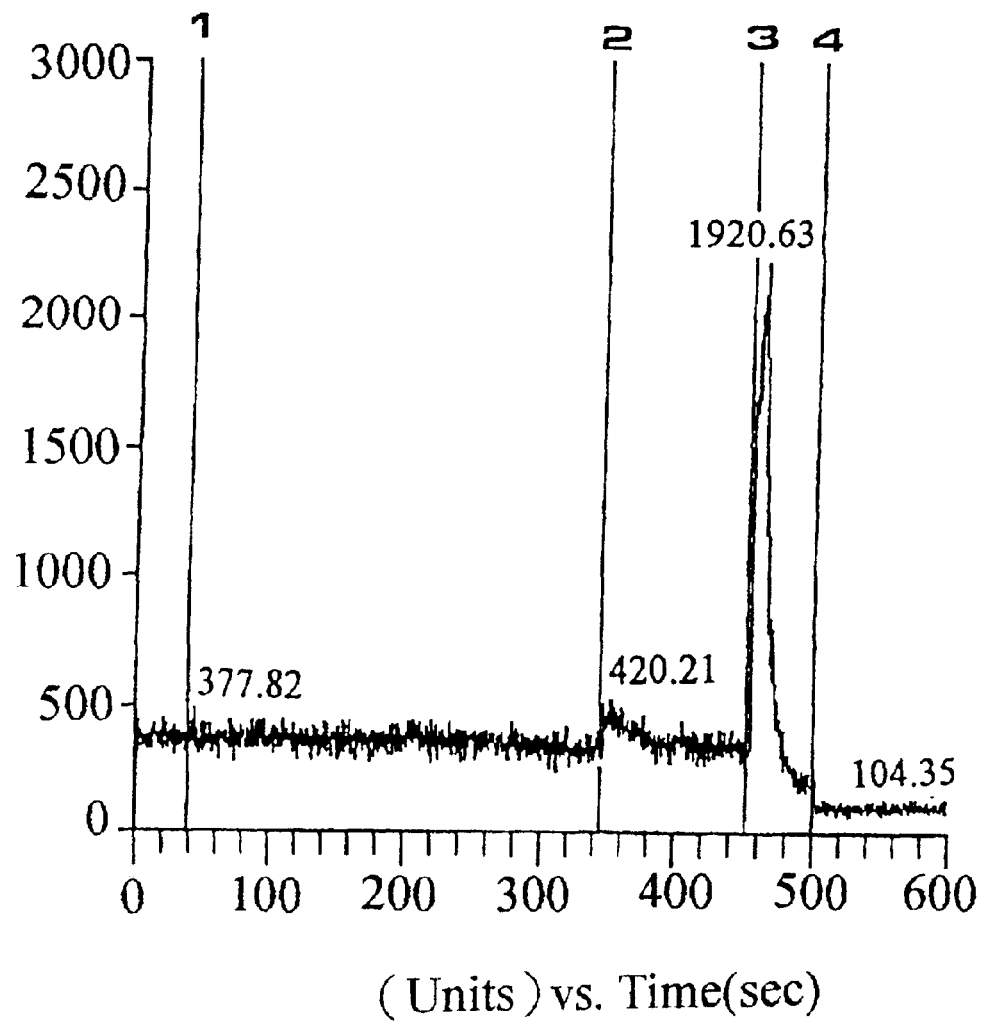
Figure 27:
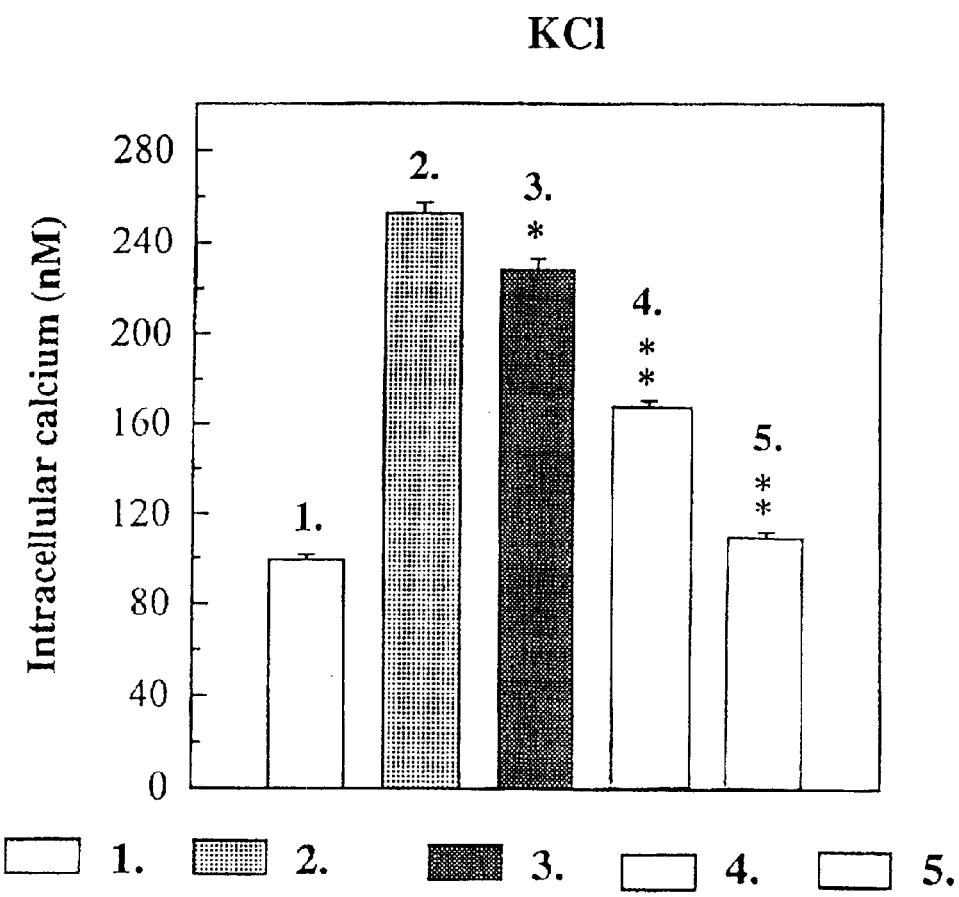
Figure 28:
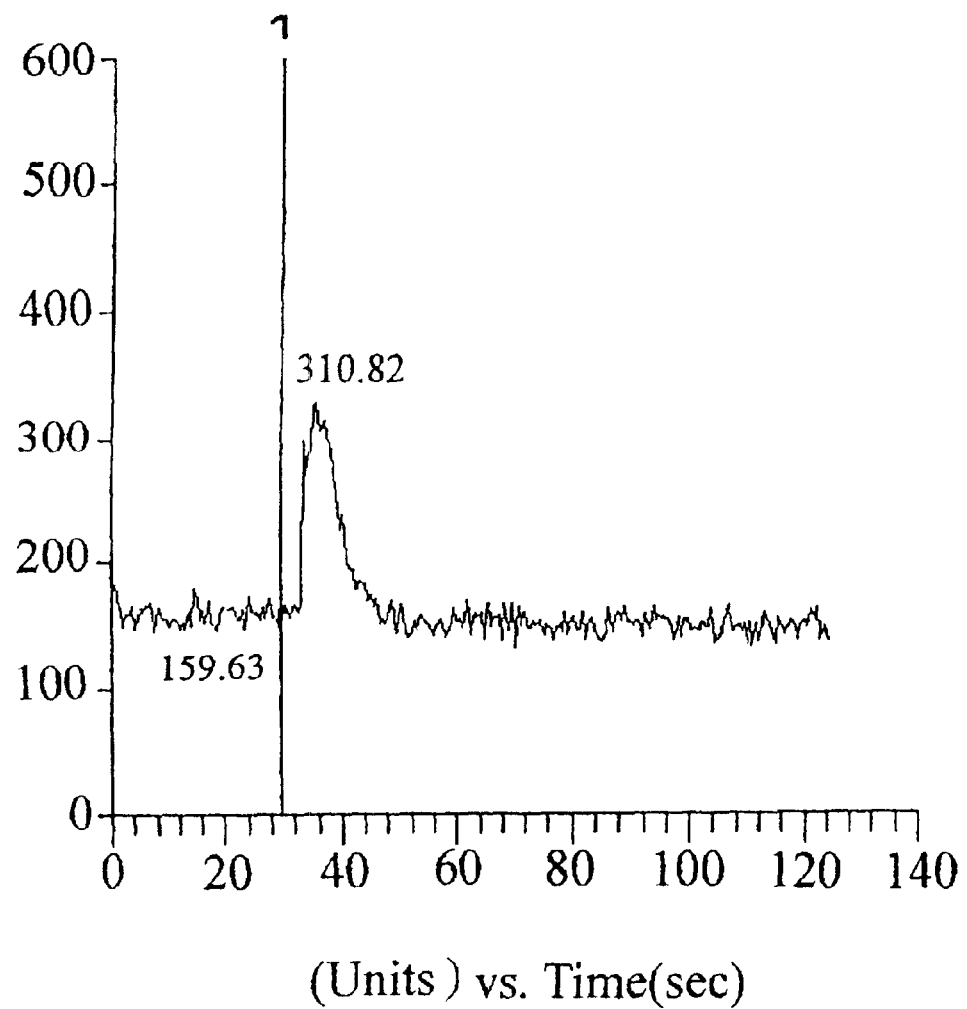

FIG. 25 illustrated fluorescence detection of calcium ion.
1 . . . 50 mM potassium chloride
2 . . . $10^{-4}$ M A23187
3 . . . 5 mM EDTA FIG. 26 illustrated fluorescence detection of calcium ion.
1 . . . $10^{-6}$ M compound 1
2 . . . 50 mM KCl
3 . . . $10^{-4}$ M A23187
4 . . . 5 mM EDTA FIG. 27 illustrated fluorescence detection of calcium ion.
1 . . . control
2 . . . 50 mM potassium chloride
3 . . . $10^{-8}$ M compound 1+50 mM potassium chloride
4 . . . $10^{-7}$ M compound 1+50 mM potassium chloride
5 . . . $10^{-6}$ M compound 1+50 mM potassium chloride FIG. 28 illustrated fluorescence detection of calcium ion.
1 . . . 10 μM Bay K8644

Figure 29:
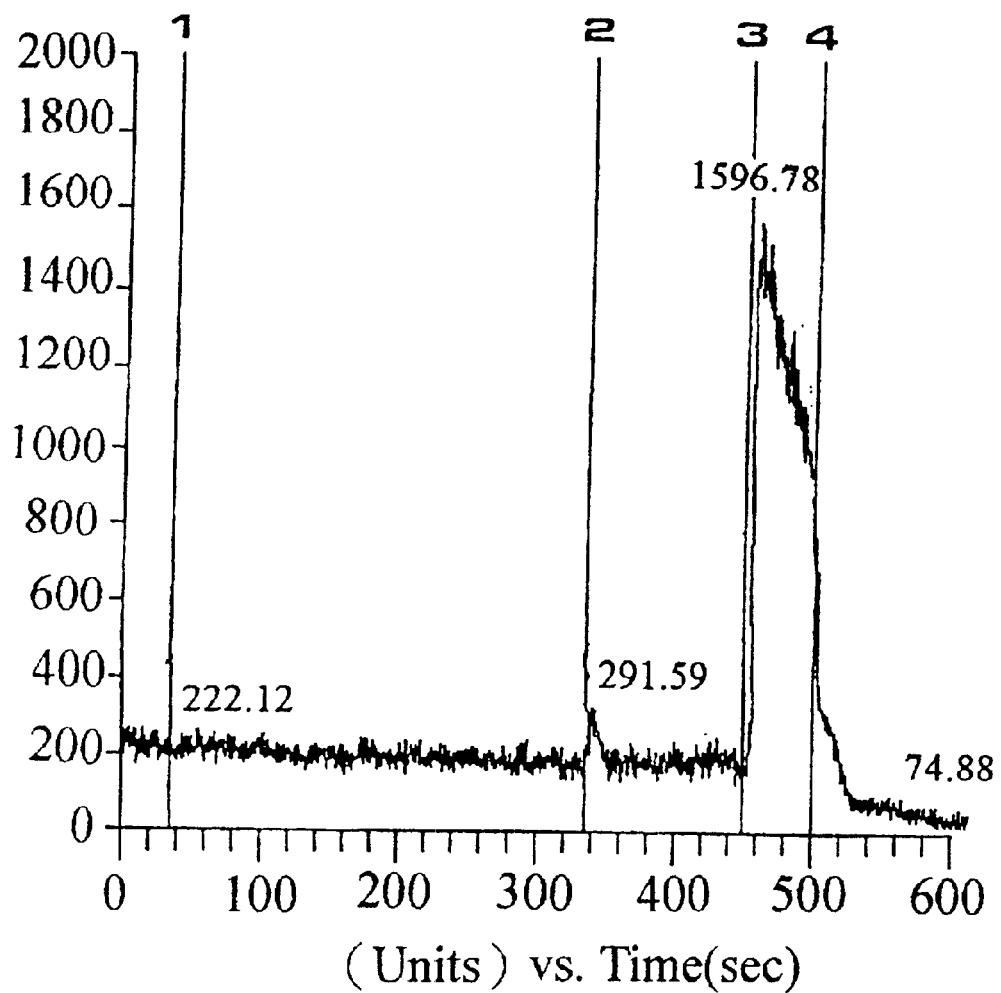
Figure 30:
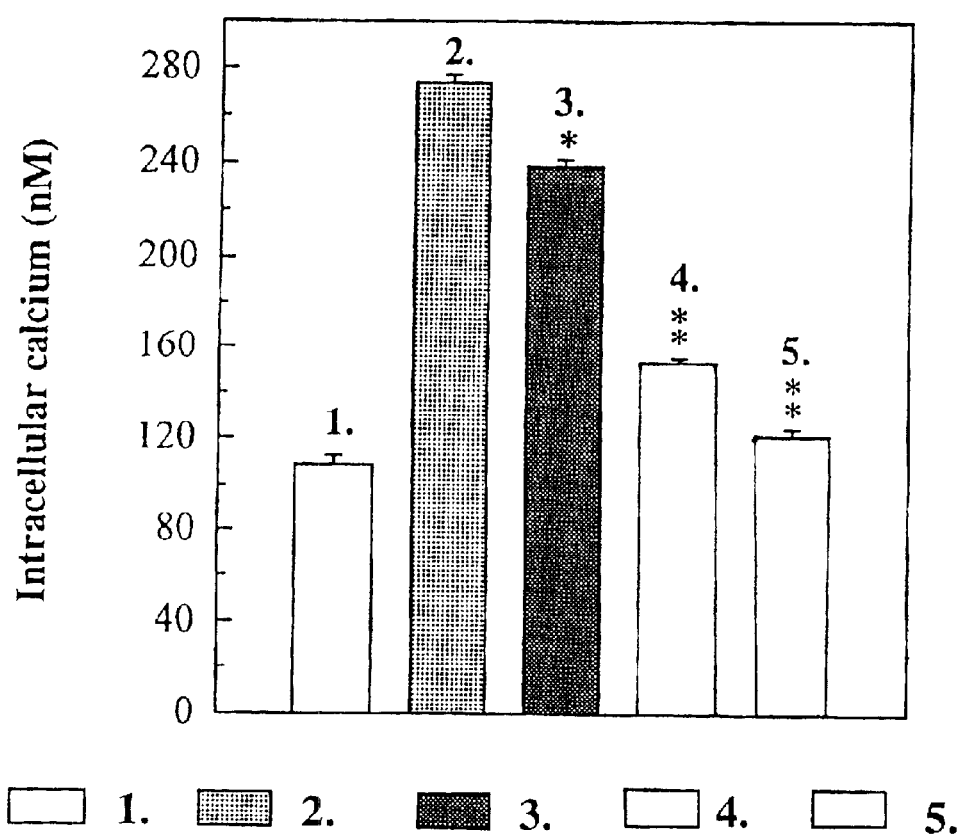

FIG. 29 illustrated fluorescence detection of calcium ion.
1 . . . $10^{-6}$ M compound 1
2 . . . 10 μM Bay K 8644
3 . . . $10^{-4}$ M A23187
4 . . . 5 mM EDTA FIG. 30 illustrated fluorescence detection of calcium ion.
1 . . . control
2 . . . 10 μM Bay K8644
3 . . . $10^{-8}$ M compound 1+10 μM Bay K8644
4 . . . $10^{-7}$ M compound 1+10 μM Bay K8644
5 . . . $10^{-6}$ M compound 1+10 μM Bay K 8644

DETAILED DESCRIPTION OF THE INVENTION

The invention disclosed some 1,4-dihydropiridine derivative compounds whether chemically with guaiacoxypropanolamine and/or phenoxypropanolamine moiety.

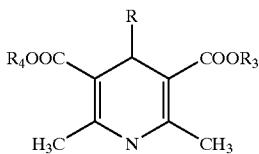

I

The compounds of 1,4-dihydropiridine derivative has the formula I, wherein R selected from four groups as follow:

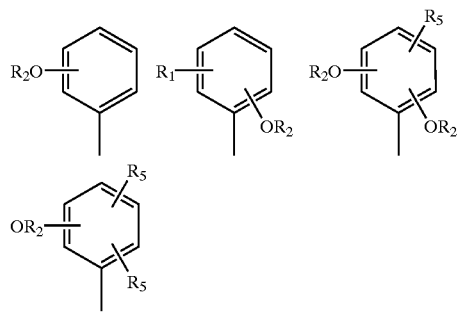

$R_1$ selected from H, X, $NO_2$, saturated $C_1$–$C_6$ alkyl group, unsaturated $C_1$–$C_6$ alkyl group, $R_2$ selected from H, $CH_3$, and the group of

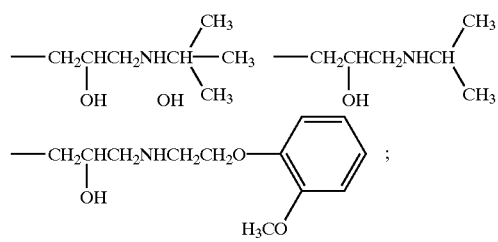

$R_3$ and $R_4$ are individually selected from saturated $C_1$–$C_6$ alkyl group, and unsaturated $C_1$–$C_6$ alkyl group; $R_5$ selected from OH, saturated $C_1$–$C_6$ alkyl group, and unsaturated $C_1$–$C_6$ alkyl group.

The 1,4-dihydropiridine derivative chemically with guaiacoxypropanolamine or phenoxypropanolamine moiety, which has formula I as the main structure, adopts the method for compound synthesis as shown in FIG. 2, which could be roughly differentiated into 4 types.

Prepared Method of 1,4-dihydropiridine Derivative Compounds

Method 1

4-hydroxy-3-methoxy-1-benzaldehyde was dissolved in ethanol with sodium hydroxide solution. After reacted with epichlorohydrin, decompressed to condense and crystallized, N-[4-(2,3-epoxy-propoxy)-3-methoxy]-1-benzaldehyde was obtained. Then with tert-butylamine to undergo amination, N-{4-[2-hydroxy-3-(tert-butylamino) propoxy]-3-methoxy}-1-benzaldehyde was obtained. By adding methylacetoacetate, Ethanol, and concentrated $NH_3$ solution to N-{4-[2-hydroxy-3-(tert-butylamino)propoxy]-3-methoxy}-1-benzaldehyde, well mixed then heat under reflux; directly decompressed to condense and Ethanol removed, the remaining solution was mixed with saturated $Na_2CO_3$ solution, and extracted with $CHCl_3$ and water. Then it was purified by column chromatography, and repeatedly re-crystallized the solid to obtain compound 1.

Say the amination, if 2-methoxy-1-oxyethylamino benzene is used, with similar procedure as the above mentioned, purified compound 2 will be obtained. On the other hand, if the material methylacetoacetate is replaced with ethylacetoacetate and the procedure remained as the above mentioned, purified compound 3 will be obtained.

Method 2

2-chloro-4-hydroxy-benzaldehyde was dissolved in ethanol with sodium hydroxide solution. After epichlorohydrin reacted; decompressed to condense and crystallized, N-[4-(2,3-epoxy-propoxy)-2-chloro]-1-benzaldehyde was obtained. Then with N-{4-2-methoxy-1-oxyethylaminobenzene to undergo amination, N-{4-[2-hydroxy-3-(2-methoxy-1-oyxethylamino-benzene) propoxy]-2-chloro}-1-benzaldehyde was obtained.

By adding ethylacetoacetate, ethanol, and concentrated $NH_3$ solution to N-{4-[2-hydroxy-3-(2-methoxy-1-oxyethylamino-benzene)propoxy]-2-chloro}-1-benzaldehyde; well mixed then heat under reflux; directly decompressed to condense and ethanol removed, the remaining solution was mixed with saturated $Na_2CO_3$ solution and extracted with $CHCl_3$ and water. Then it was purified by column chromatography, and re-crystallized the solid to obtain compound 7.

Method 3

When 5-Chlorosalicylaldehyde was dissolved in ethanol with sodium hydroxide solution, and undergone epichlorohydrin reaction; decompressed to condense and crystallized, N-[2,3-epoxypropoxy]-5-chloro]-1-benzaldehyde was obtained: Then with tert-butylamine to undergo amination, N-{2-[2-hydroxy-3-5 (tert-butylamino)propoxy]-5-chloro}-1-benzaldehyde was obtained. By adding ethylacetoacetate, ethanol, and concentrated $NH_3$ solution to N-{2-[2-hydroxy-3-(tert-butylamino)propoxy]-5-chloro}-1-benzaldehyde; well mixed then under reflux; directly decompressed to condense and Ethanol removed, the remaining solution was mixed with saturated $Na_2CO_3$ solution and extracted with $CHCl_3$ and water. Then it was purified by column chromatography, and re-crystallized to obtain compound 4.

When amination, if n-butylamine and 2-methoxy-1-oxyethylaminobenzene is used separately, with similar procedure as the above mentioned, purified compound 5 and compound 6 will be obtained.

Method 4

When 5-nitrosalicylaldehyde was dissolved in ethanol with sodium hydroxide solution, and undergone epichlorohydrin reaction; decompressed to condense and crystallized, N-[2-(2,3-epoxypropoxy]-5-nitro]-1-benzaldehyde was obtained. Then with tert-butylamine to undergo amination, N-{2-[2-hydroxy-3-(n-butylamino)propoxy]-5-chlorol}-1-benzaldehyde was obtained. By adding ethylacetoacetate, Ethanol, and concentrated $NH_3$ solution to N-{2-[2-hydroxy-3-(tert-butylamino)propoxy]-5-chlorol}-1-benzaldehyde; well mixed then reflux; directly decompressed to condense and Ethanol removed, the remaining solution was mixed with, saturated $Na_2CO_3$ solution and extracted with $CHCl_3$ and water. Then it was purified by column chromatography, and re-crystallized to obtain compound 8.

When amination, if 2-methoxy-1-oxyethylaminobenzene is used, with similar procedure as the above mentioned, purified compound 9 will be obtained.

2-methoxy-1-oxyethylaminobenzene could be prepared by adding sodium hydroxide to warm mixture of 2-methoxyphenol and ethylene dibromide. After continuous reflux; decompressed to condense and crystallized, 2-methoxy-1-oxyethylbromide benzene is obtained.

2-methoxy-1-oxyethylbromide benzene and potassium phthalimide were mixed, and the mixture dissolved in dimethylformamide. With continuous reacted the mixture and stay overnight, 2-methoxy-1-oxyethylphthalimide benzene was obtained after re-crystallization. Warming 2-methoxy-1-oxyethyl phthalimide benzene and hydrazine hydrate will result in 2-methoxy-1-oxyethylaminobenzene.

After purification and crystallization, the products are individually tested for their physio-chemical information, including element analysis; MS, IR, $^1$H-NMR ($CDCl_3$), and UV etc. Appropriate experimental models are used to evaluate their pharmacological activities, thus ascertain the compound's activity.

The compound of this invention will include various excipients; carriers or diluents and pharmaceutically approved pH of processed salts in accordance to necessity to form composition with therapeutic efficacy. Such pharmaceutical preparation could be in solid form for oral and rectum administration; liquid form or non-intestinal injection form; or ointment form for direct application on affected part. Such solid forms are manufactured according to common pharmaceutical preparation methods, which will include disintegrant like starch; sodium carboxymethyl cellulose, adhesive like ethanol; glycerine, or magnesium stearic acid; lactose to make into pharmaceutical preparation like tablets or filled into capsules or suppository. Solution or saline that include this invention compound as ingredient could use buffers of phosphoric nature to adjust the pH to suitable level, before adding adjutant; emulsifier to produce injection dose or other liquid preparation. This invention compound or pharmaceutical manufacturing could mixed synthetic acid salts with various fundamental preparations to form ointments according to known pharmaceutical manufacturing methods. Pharmaceutical compounds manufactured with this invention compound being the major ingredient could be used on mammals to produce the efficacy of this main ingredient. General dosage could be adjusted according to the degree of symptoms, and normally a person will require 10 to 100 mg each time, three times per day.

Pharmaceutical Activity

This invention compound has been proven by the following pharmaceutical experiments that it has, β receptor and calcium ion entry blocking agent; selectivity towards integrated β-adrenoceptor; and whether has intrinsic sympathomimetic activity, ISA; such type of compounds has tracheal dilation and vasorelaxant effects. Laser cell detector (ACAS 570) was used to determine the changes in the cell calcium ion concentration of smooth muscle cell line A7r5.

Heart Rate and Blood Pressure in Living Rat

Male Wistar rats, weighing 200~300 g were abdominal anaesthetized with pentobarbital sodium. Tracheal was cannulated to maintain normal respiration. Polyethylene tube was inserted into the left femoral vein to facilitate drug administration. A 3-way stopcock was used, with one end connected to a syringe for drug injection, while the other end was connected to the syringe filled with physiological saline. The latter was used to prevent residual drugs in the polyethylene tube after injection, which would affect experimental accuracy.

The right femoral artery was also inserted with polyethylene, and a 3-way stopcock was used tool, where one end was connected to heparin solution to prevent embolism. The other end was connected to a Disposable Diaphragm Dome, TA1019, and linked to a transducer. Through an amplifier, a recorder recorded the overall and average arterial pressure; heart rate to evaluate the effect of drug on blood pressure and heart rate. Different concentrations 0.1; 0.25; 0.5; 1.0; 2.0 mg/kg of compound 1 were given to the rats via femoral vein and the differences in the heart rate and blood pressure were compared. Furthermore in another group, compound 2, 3, 4, 5, 6, 7, 8, and 9 of concentration 1.0 mg/kg were separately given to different rats via femoral vein, and the differences in the heart rate and blood pressure were compared.

RESULTS

Intravenous injection of different concentration of compound 1 produced a continuous dose-dependent blood pressure lowering effect without increasing heart rate for approximately 1 hour in normotensive rats (FIGS. 4 (a)-(e)). In this experiment, intravenous injection of 0.5 mg/kg of nifedipine produced a significant blood pressure lowering effect, accompanied by reflex tarchycardia (FIG. 5 (b)). However, such observation was not found in compound 1 (FIG. 5 (a)), instead, a decrease in heart rate was shown, thus could prevent reflex tarchycardia side effect produced by calcium ion entry blocking agent of 1,4-dihydropiridine nature. The effects of compound 1-9 on heart rate and blood pressure were shown in Table 1.

Atrium; Tracheal Experiments on Isolated Rat Tissues

The methods published by Chen, I. J et. al. in Gen Pharmacol. 24, pp. 1425–1433 (1993) and by Sheu, M. M. et. al in Pharmacology 54, pp. 211–224 (1997) were referenced and modified.

The entire heart of rat was removed immediately after the rat was sacrificed and the blood drained by incised carotid arteries, and placed in Kreb-Henseleit solution equilibrated to a mixture of 95% $O_2$ and 5% $CO_2$ at room temperature (20~25° C.). The right and left atria were then separated. The spontaneously-beating right atria was clipped on both end by heart shaped clips, where one end was fixed at the bottom of 10 ml of tissue bath made of physiological saline solution, and temperature maintained at 37° C. The other end of the atria was connected to a force transducer, and isometric contractions and beating rate of the right atria were recorded by COULBOURN AT-High-Speed Video Figure. After the samples were given 250 mg of contractions and reach equilibrium the following experiments were carried out:

(a) β-adrenoceptor Blocking Action

When the spontaneously beating rate of right atria reached a certain stability, cumulative administration of L-isoproterenol from $1\times10^{-10}$~$3\times10^{-10}$ M caused the heart rate to increase continuously, and a cumulative dose-response curve was obtained. Then the L- isoproterenol was thoroughly washed off with Kreb's solution to recover the right atria's heart rate stability. After the equilibrum was reached again for at least 60 minutes, different concentrations ($10^{-7}$, $10^{-6}$, $10^7$ M) of compound 1 were added. 30 minutes later, cumulative administration of L-isoproterenol from $1\times10^{10}$~$3\times10^{-10}$ M were carried out again, and another new cumulative dose-response curve was obtained. Administration of L-isoproterenol started from concentration $1\times10^{-3\times10^{-10}}$ M, and the concentration was raised 0.5 log each time for a total of six times. Cumulative administration interval was when the previous concentration reached its greatest effect, the next concentration would be immediately given. The time interval was approximately 3~5 minutes, and the $EC_{50}$ value could be obtained. From Schild plots, the $pA_2$ of compound 1 could be found. In other groups of rats, after separate administration of compound 2, 3, 4, 5, 6, 7, 8, and 9, their $pA_2$ values were obtained.

(b) Calculation of $pA_2$ Value

According to the method mentioned by Arunlakshana, O. et al. in Br. J. Pharmacol. 14, pp. 48–57 (1959), which used the logarithm values of compound concentration testings as the x-coordinates, and the logarithm values of blocking agent of similar effect and (dose ratio)$^{-1}$ as the y-coordinates, the data obtained were plotted into Figures and the slope of regression found. From x-coordinates of the line of regression, the intercept value was found, which is the $A_2$ value of the compound under testing. The equation is as follows:

$$pA_2 = -\text{Log } KB \text{ Log } (DRADJ-1) = n \text{ log}[B] - \text{Log}KB$$

$$DRADJ(\text{dose ratio adjusted}) = \frac{DR(\text{dose ratio})}{CF(\text{correction factor})}$$

[B]=Test compound concentration in moles
KB:equilibrium dissociation constant
n:value of slope
DR:test $EC_{50}$ divided by control $EC_{50}$
CF:$EC_{50}$ of second or third control groups divided by EC50 of first control group (c) Effect of compound on the Increase of Spontaneous Beating in Right Artrium Caused by $CaCl_2$ The right atrium of the rats was allowed to equilibrate in Kreb's solution for at least 60 minutes. When the spontaneous beating rate had reached a certain stability, $CaCl_2$ of different concentrations (3.0, 6.0, and 9.0 mM) were cumulatively administered, and the changes in the spontaneous beating of right artrium were observed. Then the right atrium was thoroughly washed with Kreb's solution for several times and re-equlibrated for at least 60 minutes before different concentrations ($10^{-7}$, $10^{-6}$, and $10^{-5}$ M) of compound 1 were administed. 30 minutes later, different concentrations (3.0, 6.0, and 9.0 mM) were cumulatively administed, and the changes in the spontaneous beating of right artrium were observed again. The effect of $CaCl_2$ on the changes of spontaneous beating in right artrium were compared with and without the presence of compound 1.

(2) Experiments on the Isolated Left Atrial Tissue of Rat

The inspontaneously-beating left atrial tissue was obtained from rat's isolated right atrial tissue experiments. Under similar conditions, contractions were induced in the right atria by approximately 1 volt of square waves which had a wave width about 1 msec wider than the threshold voltage. The contraction rate was 1 Hz and the resting tension 0.5 gm. After 60 minutes of equilibration, the following experiments were performed:

(a) Completion of cumulative concentration-response curve:similar to experimental method on isolated right atrium;

(b) Calculation of pA2 value:similar to calculation method on isolated right atrium.

Results

Effect of Compound 1 on β-adrenoreceptor ($\beta_1$) Activity

Using the spontaneously beating function of Wistar rat's isolated right atrium and cumulatively administered different dosages ($1 \times 10^{-10} \sim 1 \times 10^{-6}$ M) of L-isoproterenol resulted in continuous increment of heart rate, where a cumulative dose-response curve was obtained. As shown in FIG. 6, different concentrations ($10^{-6}$, $10^{-5}$, and $10^{-6}$ M) of compound 1 could competitively block the heart rate increment effect of L-isoproterenol, at the same time, the cumulative concentration-response curve of L-isoproterenol indicated a dose-dependant movement from left to right.

Furthermore, by electrically excite the Wistar rat's isolated left atrium before cumulative administed L-isoproterenol could increase contractility. Similarly, as shown in FIG. 7, different concentrations ($10^{-6}$, $10^{-5}$ and $10^{-6}$ M) of compound 1 could competitively block the heart contractility increment effect of L-isoproterenol, at the same time, the cumulative concentration-response curve of L-isoproterenol indicated a dose-dependant movement from left to right.

The $pA_2$ value of compound 1 in Wistar rat's isolated right atrium experiment was 7.21±0.32; and the $pA_2$ value left atrium contractility experiment was 6.91±0.26. The detailed values of $pA_2$ and rate of regression slope of the other compounds were indicated in Table 2.

(3) Experiments on Guinea Pig's Isolated Tracheal

Guinea pigs of weight between 300~500 gm were used. 18~24 hours before the experiment, 5 mg/kg of reserpine was injected via abdominal cavity to prevent the discharge of catecholamines, as suggested by O'Donnell and Wanstall (1979), due to the administration of phenoxybenzamine during the experimental process. After the guinea pigs were sacrificed, a slit was made along the neck, and a portion of tracheal approximately 4 cm long was removed. The tracheal was then placed in Kreb's solution aerated with a mixture of 95% $O_2$ and 5% $CO_2$ and maintained at room temperature. After the surrounding tissue was carefully removed, the tracheal was cut into spiral shape with every turn having 3~4 cartilage segments, and divided according to the method suggested by Constantine (1965). The two ends of the tracheal were clamped with frog-heart shaped clamps, one end was fixed at the bottom of tissue bath filled with 20 ml of Kreb's solution, maintained at 37° C., while the other end was connected to a force transducer. Through a COULBOURN AT-High-Speed Videograph, long isometric contractions were recorded. After the sample was given 1.5 gm of tension and equilibrated, the following experiments were performed:

(a) Cumulative Concentration Response Curve

In the experiment, tracheal was first treated with 50 μm phenoxybenzamine for 30 minutes to prevent extraneuronal uptake, and reduce L-isoproterenol effect suggested by O'Donnell and Wanstall (1976). Then the tracheal was repeatedly washed with Kreb's solution for 20 minutes and 10-6 M of carbochol was added to cause contraction in the guinea pig's tracheal. When the contraction reached the maximum, every division of tracheal was used to complete two concentration response curve of L-isoprotemol, one of them without administration of test compound and used as control; while the other curve was administered with compound 1 for 30 minutes before concentration response curve was completed. This is the test group.

(b) Calculation of $pA_2$: Similar to the Calculation Method for Isolated Right Atrium Experiment.

Results

Effect of compound on, β-adrenoreceptor ($β_1$) activity $10^{-6}$ M of CARBACHOL was used to cause contraction in guinea pig's isolated tracheal. When it reached stability, cumulative administration of L-isoproterenol was used to obtain tracheal tension-relaxation curve. As shown in FIG. 8, treatment with $10^{-6}$, $10^{-5}$, and $10^{-6}$ M of compound 1 prior experiment could competitively block the effect of L-isoproterenol. The cumulative concentration-response curve of L-isoproterenol blocking indicated a dose-dependant movement from left to right. The $pA_2$ value of compound 1 in guinea pig's isolated tracheal experiment was 7.09±0.54. The detailed values of $pA_2$ and rate of regression slope of the other compounds were indicated in Table 2.

(4) Discussion on the Direct Effect of Wistar Rat's Isolated Atria

With reference to the method suggested by Kaumann, A. J. et. al. in Naunyn-Schmiedeberg's Arch. Pharmacol 311, pp. 205–218 and pp 237–248 (1980). Wistar rats of weight between 200~300 gm were used. 18~24 hours before the experiment, 5 mg/kg of reserpine was injected via abdominal cavity to remove all endogenous catecholamines. Prior experiment, Wistar rats were sacrificed, the heart was immediately removed and placed in Kreb's solution aerated with air mixture and maintained at room temperature. The right and left atria were carefully separated. Then in accordance to the above mentioned experimental method, the effects of cumulative administration of compound 1 ($10^{-10}$ M~$3\times10^{-6}$ M) on right atrium were recorded.

Results

The Selectivity of Compound 1 on, $β_1:β_2$ types of β-adrenoreceptors $β_1$ type: The selectivity ratio off $β_1$ type adrenoceptor was obtained from the negative logarithm of the average $pA_2$ difference between right atrium and tracheal. This was in accordance to the method published by Baird, J. R. C. et. al. in J. Pharm. Pharmacol 24 pp. 880–885 (1972). The effect of compound 1 on right atrium was 1.32× of tracheal; the effect of VANIDILOL on right atrium was 0.98× of tracheal; while the effect of PROPRANOLOL on right atrium was 1.7× stronger than tracheal. This indicates that compound 1 is similar to VANIDILOL and PROPRANOLOL in that they are non-selective on the type of β-adrenoceptor.

(5) Discussion of the Direct Effect of Guinea Pig's Isolated Tracheal

With reference to the method suggested by Kaumann, A. J. et. al. in Naunyn-Schmiedeberg's Arch. Pharmacol 311, pp. 205–218 and pp.237–248 (1980). guinea pigs of weight between 350~500 gm were used. 18~24 hours before the experiment, 5 mg/kg of reserpine was injected via abdominal cavity to remove all endogenous catecholamines. Prior experiment, guinea pigs were sacrificed, the tracheal was immediately removed and placed in Kreb's solution aerated with air mixture and maintained at room temperature of 22~25° C. The evaluation of the tracheal's endogenous activity was performed with modification according to the method suggested by Tesfamariam, B. et. al. in Br. J. Pharmacol 112, pp. 55–58 (1994). Firstly, compound 1 of concentrations $10^{-7}$; $10^{-6}$; $10^{-5}$M were cumulatively added into the tissue trough to observe their effects on tracheal. Then the tissue was repeatedly washed with Kreb's solution. After the tissue had been re-equilibrated for 60 minutes, ICI 118, 551 were administed. After treatment for 30 minutes, compound 1 of similar concentration was administered, and the intrinsic sympathomimetic activity of tracheal was observed.

Results

The Intrinsic Sympathomimetic Activity of Compound 1

After cumulatively increase the concentrations of compound 1, the changes in the Wistar rat's isolated; reserpine pretreated right atrium beating rate and left atrium isometric contractions were observed. As shown in FIG. 9 and FIG. 10, the cumulative administration of L-isoproterenol would dose-dependently increase the right atrium beating rate and left atrium isometric contractions. Compound 1 could not increase the beating rate and isometric contractions, instead, when the concentration reached $10^{-5}$ M or above, there was blocking effect on beating rate and isometric contractions. PROPRANOLOL could retard the beating rate and isometric contractions., and this retardation is proportionally related to the concentration increment. When the dosage concentration is increased to $10^{-4}$~$10^{-3}$ M, it could inactivate or unexcited the tissue. However, at $3\times10$-4M concentration, ATENOLOL almost does not have atrial blocking effect. Furthermore, when guinea pig's isolated; reserpine pretreated tracheal was cumulatively administered with $10^{-10}$~$3\times10^{-6}$ M L-isoproterenol or $10^{-10}$~$3\times10^{-6}$ M VANIDILOL; $10^{-10}$~$3\times10^{-6}$ M nifedipine; and $10^{-10}$~$3\times10^{-6}$ M compound 1, they could individually caused dose-dependant tracheal relaxation effect.

However, as shown in FIG. 10, cumulative administration of PROPRANOLOL did not produce any relaxation effect. To prove that whether tracheal relaxation effect induced by compound 1 is related to s $β_2$-adrenoceptor, guinea pig's isolated tracheal was pretreated with $β_2$-adrenoceptor's selective blocking agent, ICI118, 551 at concentrations $10^{-8}$, $10^{-9}$, and $10^{-10}$M for 30 minutes. As shown in FIG. 12, the effect of competitive blocking agent, compound 1 had been observed, and the cumulative concentration-dependant curve of compound 1 was concentration-dependently shifting parallel to the right. Furthermore, as shown in FIG. 13, the tracheal relaxation effect of cumulatively administed nifedipine at concentrations $10^{-10}$~$3\times10^6$ M on guinea pig's isolated and reserpine pretreated tracheal was not blocked by $10^{-8}$ M of ICI 118, 551. This showed that the tracheal relaxation effect produced by nifedipine was not related to $β_2$-adrenoceptor.

(6) Experiment on the Wistar Rat's Isolated Thoracic Aorta

After sacrificing Wistar rat of weight between 300–500 gm, the thoracic aorta was immediately removed and placed in cold Kreb's solution. The fatty connecting tissue surrounding the vessel wall was removed and the thoracic aorta was cut into rings of length 5 mm. The two ends of each ring was pieced and fixed with "Z" shaped platinum wires. Then the thoracic aorta was suspended in 10 ml of tissue bath, aerated with air mixture (95% $O_2$+5% $CO_2$) and maintained at 37° C., where one end was fixed at the bottom of tissue trough, the other end connected to force transducer to record the long contraction via recorder. The sample was given 1 gm of tension and equilibrated for 60 minutes before the following experiments were carried out:

(a) The Effect of Compound 1 on the Thoracic Aorta Contraction Caused by 75 mM KCl After thoracic aorta had reached equilibrium in the tissue trough, the normal Kreb's solution in the trough was replaced with 75 mM KCl solution to induce vasoconstriction. When the results had been recorded for at least 35 minutes, the aorta was repeatedly rinsed with normal Kreb's solution. After the aorta had re-equilibrated and at least rested for 60 minutes, different concentrations ($10^{-8}$, $10^{-7}$, $10^{-6}$, and $10^{-5}$M) of compound 1 were separately added. 30 minutes later, 75 mM KCl was added again to induce vasoconstriction. This method was used to compare the differences in contraction induced by 75 mM KCl on thoracic aorta pre-treated and non-treated with compound 1.

Results

Effect of Compound 1 on Isolated Guinea-pig Aorta

The effect of compound 1 on the thoracic aorta contraction caused by 75 mM KCl. The Wistar rat's isolated thoracic aorta was contraction induced by 75 mM of concentrated Potassium solution. After vasoconstriction had reached stability, different concentrations ($10^{-8}$, $10^{-7}$, $10^{-6}$, and $10^{-5}$ M) of compound 1 as stated in FIG. 23 and FIG. 25 were added, which could induce dose-dependant vasoconstriction. Furthermore, the contraction effects of 10-8M of compound 1-9 were indicated on Table 1.

(b) The Effect of Compound 1 on BayK8644 Pretreated Thoracic Aorta 0.1 M of BayK8644 was first added into the tissue trough. 10 minutes later, 75 mM of concentrated Potassium solution was added to induce thoracic aorta contraction. When vasoconstriction had reached stability, different concentrations of ($10^{-8}$, $10^{-7}$, $10^{-6}$, and $10^{-5}$M) compound 1 were separately added. The effects of aorta contraction induced by concentrated Potassium solution were observed.

Results

The Effect of BayK 8644 on Vasorelaxantion of Compound 1

After the thoracic aorta was pre-treated with 0.1 $\mu$M of BayK8644 for 10 minutes, concentrated Potassium solution was added to induce vasoconstriction. When the vasoconstriction reached stability, compound 1 of concentrations $10^{-8}$, $10^{-7}$, $10^{-6}$, and $10^{-5}$ M were added. The results was shown in FIGS. 24 and 25 which indicated that pre-treatment with BayK8644 would affect vasoconstriction function of compound 1.

(7) Discussion on Characteristics of Receptor Binding (a) Preparation of Cell Membrane at 4° C.

The method of Muzzin et. al. (1992) was modified and referenced. The heart and lung of rat were removed and placed in cold Tris buffer. Then the atria and lung were separated and weighed, before placing in cold Tris buffer with volume 20× their weights. Using POLYTRON homogenizer at 15 seconds each time to crushed the tissue for 3~4 times before homogenization. The homogenized liquid was press filtered through gauze, and the filtered liquid was centrifuged at 700 gm for 12 minutes. The centrifugal fluid was again centrifuged at 10,000 gm for 12 minutes. The second centrifugal fluid was centrifuged for the third time at 29,000 gm for 15 minutes. The pellet finally obtained was re-suspended in Tris buffer as little as possible. Then the method of Brodford (1976) was adopted, where BSA was used as a standard, and protein assay dye was used to determine the protein content in the membrane. Finally, the protein concentration was diluted with Tris buffer to maintain 200~250 $\mu$g protein per 100 $\mu$l.

| Tris buffer | pH 7.4 |
|---|---|
| Sucrose | 250 mM |
| Tris buffer | 50 mM |
| $MgCl_2$ | 1 mM |

(b) Binding Assay on Receptor

The methods of Porzig et. al. (1982); Petrus (1988); and Muzzin et. al. (1974) were adopted with modifications. 100 $\mu$l of membranes; 50 $\mu$l of [$^3$H]CGP-12177; 50 $\mu$l of test compound in various concentrations; eg. PROPRANOLOL, compound 1, and VANIDILOL were mixed to obtain a final volume of 250 $\mu$l. This mixture was placed under 25° C. vibration and reacted for 60 minutes. After reaction, 1 ml of cold Tris buffer was added to terminate the binding reaction. Then Millipore filtration manifold and Whatman GF/C glass fiber were used for rapid press filtration, and 5 ml of cold Tris buffer was used to rinse the filtrate three times. After the filter paper with the filtrate was dried in a 60° C. oven for 3 hours, 5 ml of scintillation fluid was added, and Beckman LS6500 rackbeta liquid scintillation counter was used to determine the strength of radioactivity.

(8) Discussion on the Characteristics of Calcium Ion Receptor Binding (a) Preparation of Cell Membrane at 4° C.

The method of Tamazawa et. al. (1986) was modified and referenced. The cerebral cortex of rat was removed and placed in cold 0.85% NaCl solution. Then the cortex was weighed, before placing in cold 50 mM Tris-HCl solution and 10 mg EDTA (pH 7.7) with volume 9× its weight. Using POLYTRON homogenizer at 15 seconds each time to crushed the tissue for 3~4 times before homogenization. The homogenized liquid was press filtered through gauze, and the filtered liquid was centrifuged at 900 gm for 10 minutes. The centrifugal fluid was again centrifuged at 29,000 gm for 15 minutes. The pellet finally obtained was rinsed with 50 mM Tris-HCl solution and 10 mg EDTA (pH 7.7) twice before resuspended in similar Tris-HCl solution and store at −80° C. Then the method of Brodford (1976) was adopted, where BSA was used as a standard, and protein assay dye was used to determine the protein content in the membrane. Finally, the protein concentration was diluted with Tris-HCl solution to maintain at 4 mg/ml.

(b) Binding Assay on Receptor

The methods of Gould et. al. (1982) was adopted with modifications. 100 $\mu$l of [$^3$H]nitrendipine, 100 $\mu$l of Tris-HCl solution, 200 $\mu$l of membranes, 100 $\mu$l of test compound in various concentrations, PROPRANOLOL; compound 1, and VANIDILOL were mixed to obtain a final volume of 500 $\mu$l. This mixture was placed under 25° C. vibration and reacted in the dark for 60 minutes. Then Millipore filtration manifold and Whatman GF/C glass fiber were used for rapid press filtration, and 4 ml of cold Tris-HCl solution and 0.1 mM EDTA (pH 7.7) were used to rinse the filtrate four times. After the filter paper with the filtrate was dried in a 70° C. oven for 1 hours, 4 ml of scintillation fluid was added, and Beckman LS6500 scintillation counter was used to determine the strength of radioactivity.

(9) Fluorescence Determination of Intracellular Calcium Ion (a) Cell Culture Originated from American type culture collection, CRL 1446, clonal cell line A7r5 from Rockville was cultured in Dulbecco's modified Eagle's medium (DMEM) supplemented with 10% fetal bovine serum; 10000 U/ml penicillin G and 10 mg/ml streptomycin, and placed in 37° C. incubation oven with 95% $O_2$ +5% $CO_2$ aeration. Cells were subcultured weekly after detachment by using culture medium containing 1% trypsin. This stage of experiment was completed after cells reached confluence.

(b) Measurement of $[Ca^{2+}]_i$ Concentration of A7r5

The cells were prepared as mentioned above. The concentration of $[Ca^{2+}]_i$ was measured using a fluorescent indicator, fluo 3-AM, where the cells were scanned by image and line scan. Firstly, in A7r5 cell culture medium, 5 μ m of fluo 3-AM, Calbiochem USA was added to stain the cells. After incubating in 37° C. of $CO_2$ for an hour, Tyrode's solution containing calcium ions were used to rinse the cells for three times to remove excess extra-cellular Fluo 3-AM. A laser cytometer from Meridian Instruments Inc., USA) was used to measure the changes in the concentration of $[Ca^{2+}]_i$. Firstly, phase optics microscope was used to locate individual cells, then the fluorescence intensity of intracellular fluo 3-AM was determined by laser fluorescence scanning. The intensity of fluo 3-AM was measured by line scanning at 30 second interval with an argon laser at 488 mm. A computer was used to convert the fluorescent line into a pseudogrey level line, coded according to fluorescence intensity. After addition of 50 mM KCl and scanned for 125 seconds to establish a baseline, the cells were rinsed with Tyrode's solution, $10^{-8}$, $10^{-7}$, and $10^{-6}$ M of compound 1 were separately added and each scanned for 300 seconds. Finally, 50 mM KCl was added to record the changes in the concentration of $[Ca^{2+}]_i$.

The fluorescence ratio and concentration of $[Ca^{2+}]_i$ are proportionately related. The relationship between the above mentioned two items could be represented by a equation $$[Ca^{2+}] = \frac{Kd(F - Fmix)}{Fmax - F}$$

Kd is the dissociation constant 320 nM for fluo 3-AM. Adding $10^{-4}$M of nonfluoroscent $Ca^{2+}$ ionophore 4-bromo-A-23187 to the cells could obtain the Fmax value, while further addition of 5 mM EDTA to remove intra- and extra-cellular calcium ions, the Fmin could be obtained. Furthermore, using 10 μM of BayK8644, a $Ca^{2+}$ channel activator to replace the previous KCl, and with similar procedure for different concentrations ($10^{-8}$, $10^{-7}$, and $10^{-6}$ M) to observe the blocking effect of compound 1 on intracellular $Ca^{2+}$ concentration increment by BayK8644 (10 μM).

Results

Compound 1 on β-receptor Binding

As shown in FIGS. 14 and 16, using different concentrations from 0.003~80 nM of [$^3$H]CGP-12177 on dose-dependant binding research indicated that [$^3$H]CGP-12177 binding to Wistar rat's atria and lung membrane could reach saturation. Furthermore, as shown in FIGS. 14 and 16, analysis method by Scatchard (1949) was used to determine receptor affinity and number of binding position. At 25° C., the equilibrated Kd of atria and lung membranes were 0.16±0.03 and 1.75±0.50 (nM) respectively. The maximum binding density (Bmax) of receptor were 43.1±2.6, 294.5±20.4 (fmol/mg protein). These data indicated that the equation is average±standard error. The receptor binding of [$^3$H]CGP-12177 could reach stability in approximately 20 minutes and could last up to 90 minutes.

As shown in FIGS. 15 and 17, the pKi values of competitive curve of β-adrenoceptor blocking agent on Wistar rat's atrium; lung membrane receptors were listed on Table 2. For β-adrenoceptor blocking agent in blocking the binding of [$^3$H]CGP-12177 to atrial β1-receptor; lung β2-receptor, its effectiveness in sequence is PROPRANOLOL>>compound 1.

Compound 1 on Calcium Ion Blocking (a) The Effect of Compound 1 on Atrial Beating Rate Changes Induced by $CaCl_2$:

Cumulatively administered 3.0; 6.0; and 9.0 mM of $CaCl_2$ into Kreb's solution showed that atrial beating rate had a concentration dependant increment when 3.0; 6.0; and 9.0 mM of $CaCl_2$ were separately added. As shown in FIGS. 18, 22, under the presence of different concentrations ($10^{-7}$, $10^{-6}$, and $10^{-5}$M) of compound 1, increased atrial beating rate effect induced by cumulatively administered 3.0, 6.0, and 9.0 mM of $CaCl_2$ was found to be blocked, that is, under similar concentrations of $CaCl_2$, the atrial beating rate could not reach similar strength of increment.

(b) Compound 1 on Binding Research of Calcium Ion Receptor

As shown in FIG. 23, using different concentrations (0.001~10 nM) of [$^3$H]nitrendipine in dose dependant receptor binding research indicated that [$^3$H]nitrendipine binding to rat's cerebral cortex could reach saturation. Furthermore, as shown in FIGS. 14 and 16, analysis method by Scatchard (1949) was used to determine receptor affinity and number of binding position. At 25° C., the equilibrated Kd of atria and lung membranes were 0.16±0.03 and 1.75±0.50 (nM) respectively. The maximum binding density (Bmax) of receptor were 43.1±2.6, 294.5±20.4 (fmol/mg protein). These data indicated that the equation is average±standard error. The receptor binding of [$^3$H]CGP-12177 could reach stability in approximately 20 minutes and could last up to 90 minutes.

As shown in FIG. 24, the pKi values of competitive curve of calcium ion entry blocking agent on Wistar rat's cerebral cortex calcium ion were listed on Table 3. For calcium ion entry blocking agent in blocking the binding of [$^3$H] nitrendipine to cerebral cortex calcium ion receptors, its effectiveness in sequence is nifedipine>compound 1.

(c) Fluoro-measurement of Intracelluar Calcium Ion

Separately adding 50 mM KCl and 10 μM BayK8644 to A7r5 cells stained with fluo 3-AM, then the changes in the concentration of intracellular calcium ion were measured by fluoro-measurement method. As shown in FIGS. 25; 28, the results indicated that both KCl and BayK8644 could induce influx of calcium ions into A7r5 cells, thus increase the concentration of intracellular calcium ions, producing a high peak for $[Ca^{2+}]_i$. Next, the cells were separately treated with $10^{-8}$, $10^{-7}$, and $10^{-6}$M of compound 1 for 5 minutes, before addition of KCl or Bay8644. As shown in FIGS. 29; 30, the results indicated that the calcium ion influx effect of both KCl and BayK8644 had been significantly blocked, such that at this period of time there was no significant peak for $[Ca^{2+}]_i$. Among which, the blocking effect of compound 1 in preventing increment of calcium ion concentration is greater for BayK8644 than for KCl, also this blocking effect of compound 1 showed a concentration dependant curve.

EXAMPLE 1

Synthesis of Compound 1

8 gm of sodium hydroxide was dissolved in 100 ml of absolute alcohol. 1 molar of 4-hydroxy-3-methoxy-1- benzaldehyde was dissolved in the above prepared solution and mixed under room temperature. Then 5 molar of Epichlorohydrin was added and reacted under room temperature. TLC was used to ensure complete reaction. After decompression to concentrate, the concentrated liquid was purified by silica gel column chromatography, eluated by hexane:ethylacetate=1:9, concentrated under reduced pressure to obtain white coarse crystals, and then re-crystallized by hexane to obtain N-[4-(2,3-epoxypropoxy)-3-methoxy]-1-benzaldehyde.

Similar molar of N-[4-(2,3-epoxypropoxy)-3-methoxy]-1-benzaldehyde and tert-butylamine were dissolved in 100 ml of absolute alcohol, and undergone amination in slight warmth. After mixing and left overnight, a white solid crystal could be obtained. The solid crystal was re-crystallized by methanol to afford compound N-{4-[2-hydroxy-3-(tert-butylamino)propoxy]-3-methoxy}-1-benzaldehyde.

0.01M of N-{4-[2-hydroxy-3-(tert-butylamino)propoxy]-3-methoxy}-1-benzaldehyde was heated with 2.4 ml (0.02M) of methylacetoacetate; 15 ml ethanol; and 10 ml of concentrated amine solution, and reacted in 55° C. water bath for 15 hours. The solution obtained from the reaction was directly decompressed to concentrate and dehydrated to remove ethanol. The remaining solution was added with 50 ml of saturated $Na_2CO_3$ solution, and extracted repeatedly with $CHCl_3$ and water. All the organic layers obtained were dried; filtered and concentrated. The oil layer obtained was combined with ethanol-HCl mixed liquid and purified by Silica gel column chromatography (methanol: ethylacetate= 3:7). Slightly yellowish white crystals were firstly crystalized by ethylacetate, then re-crystallized by methanol:ethylacetate (1:9) to afford compound 1.

The structure of compound obtained is $C_{25}H_{36}O_7N_2 \cdot HCl$, and the molecular weight through mass spectrometer is 513. $^1$H-NMR $(CDCl_3)\delta$:1.46 (s, 9H, 3×$CH_3$), 2.33 (s, 6H, 2×$CH_3$), 3.00–3.45 (m, 2H, $CH_2$—NH), 3.65(s, 6H,CO—$OCH3$×2), 3.77 (s, 3H, $OCH_3$), 3.93–4.14 (m, 2H, Ar—$OCH_2$), 4.53 (m, 1H, CH—OH), 4.94 (s, 1H, Ar—CH<), 5.45 (brs, 1H, replaceable, —NH—), 6.33–6.87 (m, 3H,Ar), 8.33 (brs, 1H, replaceable, $CH_2$—NH—C), 9.28 (brs, 1H, replaceable, OH); IR (KBr):3360, 2950, 1710, 1655, 1440, 1380 $cm^{-1}$. MS m/s:513 (Scan FAB+) Anal. ($C_{25}H_{36}O_7N_2 \cdot HCl$) C,H,N. In accordance to the analytical data, compound 1 was found to be 4-{4-[2-hydroxy-3-(tert-butylamino)propoxy]-3-methoxy}phenyl}}-2,6-dimethyl-3,5-dicarbo methoxy -1,4-dihydro-pyridine.

EXAMPLE 2

Synthesis of Compound 2

0.2M of 2-methoxyphenol and 0.4M of Ethylene dibromide were heated till boil in a triple-necked flask, and mixed with a rod for 30 minutes. 125 ml of 1.6N sodium hydroxide was added, and heated with mixing until layers were divided. After heating overnight, TLC was used to ensure complete reaction, and $CHCl_3$ was repeatedly used to extract the organic layer.

300 ml of 2N sodium hydroxide was used to rinse the organic layer, before magnesium sulfate anhydeide was added and left overnight. Then the compound was filtered, decompressed to concentrate, and purified by silica gel column chromatography, eluated with hexane:ethylacetate= 9:1, and the first intermediate product 2-methoxy-1-oxyethylbromide benzene was thus obtained.

Using similar molar of potassium phthalimide to perform the above mentioned procedure, 2-methoxy-1-oxyethyl bromide benzene was obtained. This was dissolved in dimethyformamide, and its temperature raised to 55° C. within 5 minutes. After this temperature was maintained for 30 minutes, it was lowered to room temperature, and $CHCl_3$ was used to repeatedly extract the organic layer of the former. The layer was rinsed with 0.2N sodium hydroxide, then added with magnesium sulfate anhydride and left to rest overnight to remove residual liquid, before filtration and decompression to concentrate. Finally via crystallization, the second intermediate product, 2-methoxy-1-oxyethylphthalimide benzene was obtained.

Similar molar of 2-methoxy-1-oxyethylphthalimide benzene and hydrazine hydrate were dissolved in absolute alcohol, then brought to boil for 45 minutes. After addition of suitable amount of 18% HCl salt to produce white sediment, the solution was boiled for another hour. The compound was then filtered and rinsed with absolute alcohol. The filtrate was decompressed to concentrate and rinsed in 20% sodium hydroxide. After the organic layer was extracted by $CHCl_3$, anhydrous magnesium sulfate was added, and the layer was left to rest overnight before second filtration. With decompression to concentrate, 2-methoxy-1-oxyethylamino benzene was obtained.

8 gm of sodium hydroxide was dissolved in 100 ml absolute alcohol 1 molar of 4-hydroxy-3-methoxy-1-benzaldehyde was dissolved in the above mentioned solution. This solution was stirred under room temperature, and 5 molar of epichlorohydrin was added to react. TLC was used to determine whether the reaction was completed. The reaction solution was concentrated under reduced pressure and purified by silica gel column chromatography, eluated the column by hexane:ethylacetate=9:1, concentrated under reduced pressure, and re-crystallized by hexane to afford N-[4-(2,3-epoxypropoxy)-3-methoxy]-1-benzaldehyde.

Similar molar of 2-methoxy-1-oxyethylamino benzene and compound prepared from the above mentioned procedure were dissolved in 100 ml of absolute alcohol, and undergone amination in slight warmth. After stirring and left to rest overnight, a yellowish white solid crystal was obtained. The solid crystal was re-crystallized by methanol to afford compound N-{4-[2-hydroxy-3-(2-methoxy-1-oxyethylaminobenzene) propoxy]-3-methoxy}-1-benzaldehyde.

0.01M of N-{4-[2-hydroxy-3-(2-methoxy-1-oxyethylaminobenzene) propoxy]-3-methoxy}-1-benzaldehyde was dissolved in a solution containing 2.4 ml (0.02M) methylacetoacetate, 15 ml ethanol and 10 ml concentrated ammonia water; heated and placed in a water bath of 55° C. for 15 hours. After the reaction, the solution obtained was directly decompressed to concentrate and ethanol removed. 50 ml of saturated $Na_2CO_3$ solution was added to the remaining solution and the organic layers were extracted by $CHCl_3$ and water for several times. All the organic layers obtained were dehydrated, filtered and concentrated, then purified by silica gel column chromatography, eluated by methanol:ethylacetate=1:9 and concentrated under reduced pressure to obtain compound 2.

The structure of compound obtained, compound 2 is $C_{30}H_{38}O_9N_2$, and the molecular weight through mass spectrometer is 570. $^1$H-NMR($CDCl_3$) δ:2.26(s, 6H, 2×$CH_3$), 2.50–2.89 (m, 4H, $CH_2$—NH—$CH_2$), 3.56 (s, 6H, 2×CO—$OCH_3$), 3.68–3.74 (d, 6H, 2×$OCH_3$), 3.86–4.05 (m, 4H,2× Ar—$OCH_2$), 4.4 (m, 1H, CH—OH), 4.83(s, 1H, Ar—CH<), 6.84–7.37(m, 7H, Ar—H), 8.33 (s, 1H, replaceable, NH—). MS m/s:570 (Scan $FAB^+$) Anal. ($C_{30}H_{38}O_9N_2$)C,H,N. In accordance to the analytical data, compound 2 was found to be 4-{{N-{4-[2-hydroxy-3-(2-methoxy-1-oxyethyl-aminobenzene)propoxy]-3-methoxy}phenyl}}-2,6-dimethyl-3,5-dicarbo-methoxy-1,4-dihydropyridine.

EXAMPLE 3

Synthesis of Compound 3

8 gm of sodium hydroxide was dissolved in 100 ml absolute alcohol. 1 molar of 4-hydroxy-3-methoxy-1-benzaldehyde was dissolved in the above mentioned solution. This solution was stirred under room temperature, and 5 molar of epichlorohydrin added to react for 2 hour. TLC was used to determine whether the reaction was completed. The reaction solution was then purified by silica gel column chromatography, using hexane:ethylacetate=1:9 to eluate from silica gel column, concentrated under reduced pressure and re-crystallized by hexane to obtain N-[4-(2,3-epoxypropoxy)-3-methoxy]-1-benzaldehyde.

Similar molar of N-[4-(2,3-epoxypropoxy)-3-methoxy]-1-benzaldehyde and 2-methoxy-1-oxyethylaminobenzene were dissolved in 100 ml of absolute alcohol, and undergone amination in slight warmth. After mixing and left re-crystallized by methanol to afford N-{4-[2-hydroxy-3-(2-methoxy-1-oxyethylamino -benzene) propoxy]-3-methoxy}-1-benzaldehyde.

0.01M of N-{4-[2-hydroxy-3-(2-methoxy-1-oxyethylaminobenzene)propoxy]-3-methoxy}-1-benzaldehyde was dissolved in a solution containing 2.4 ml (0.02M) ethylacetate, 15 ml ethanol and 10 ml concentrated ammonia water; heated and placed in a water bath of 55° C. for 15 hours. After the reaction, the solution obtained was directly decompressed to concentrate and led ethanol removed. 50 ml of saturated $Na_2CO_3$ solution was added to the remaining solution and the organic layers were extracted by $CHCl_3$ and water for several times. All the organic layers obtained were dehydrated; filtered and concentrated, then the oil layer obtained was added to a ethanol-HCl mixed solution, and purified by silica gel column chromatography (eluated by methanol:ethylacetate=3:7). The eluated solution was concentrated under reduced pressure, precipitated out pale yellowish white crystals by ethylacetate, and re-crystallized by ethanol:ethylacetate=1:9 to obtain compound 3.

The structure of compound obtained, compound 3 is $C_{32}H_{42}O_9N_2$, and the molecular weight through mass spectrometer is 598. $^1$H-NMR(CDCl$_3$) δ:1.20–1.27(t, 6H,2×OCH$_2$CH$_3$), 2.33(s, 6H, 2×CH$_3$), 2.50–2.89(m, 4H, CH$_2$—NH—CH$_2$), 3.45(m, 4H, 2×CO—OCH$_2$CH$_3$), 3.78–3.84(d, 6H,2×OCH$_3$), 4.95(s, 1H, Ar—CH<), 5.73 (brs, 1H, replaceable, —NH—), 6.76–6.91(m, 7H, Ar). MS m/s:598 (Scan FAB$^+$) Anal. ($C_{32}H_{42}O_9N_2$)C,H,N. In accordance to the analytical data, compound 1 was found to be 4-{{N-{4-[2-hydroxy-3-(2-methoxy-1-oxyethyl-aminobenzene)propoxy]-3-methoxy}phenyl}}-2,6-dimethyl-3,5-dicarboethoxy-1,4-dihydropyridine.

EXAMPLE 4

Synthesis of Compound 4

8 gm of sodium hydroxide was dissolved in 100 ml absolute alcohol. 1 molar of 5-chlorosalicylaldehyde was dissolved in the above mentioned solution. This solution was stirred under room temperature, and 5 molar of epichlorohydrin was added to react. TLC was used to determine whether the reaction was completed. The reaction solution was concentrated under reduced pressure and purified by Silica gel column chromatography, using hexane:ethylacetate=1:9 to eluate, concentrated under reduced pressure, and re-crystallized by hexane to afford N-[2-(2,3-epoxy-propoxy)-5-chloro]-1-benzaldehyde.

Similar molar of N-[2-(2,3-epoxypropoxy)-5-chloro]-1-benzaldehyde and tert-butylamine were dissolved in 100 ml of absolute alcohol, and undergone amination in slight warmth. The reaction solution was concentrated under reduced pressure, purified by silica gel column chromatography and eluated by methanol:ethylacetate=1:1. Obtained eluate was further concentrated under reduced pressure and re-crystallized by methanol to afford N-{2-[2-hydroxy-3-(tert-butylamino)propoxy]-5-chloro}-1-benzaldehyde.

0.01M of N-{2-[2-hydroxy-3-(tert-butylamino)propoxy]-5-chloro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the obtained solution was directly decompressed to concentrate and remove ethanol. 50 ml of saturated $Na_2CO_3$ solution was added to the remaining solution and the organic layers were extracted by $CHCl_3$ and eater for several times. All the organic layers obtained were dehydrated; filtered and concentrated, then the oil layer obtained was added to a ethanol-HCl mixed solution, purified by silica gel column chromatography, eluated by methanol:ethylacetate=3:7, concentrated under reduced pressure, precipitated out pale yellowish white crystals, crystallized by ethylacetate then by ethanol:ethylacetate=1:9 to afford compound 4.

The structure of compound obtained, compound 4 is $C_{26}H_{37}O_6N_2Cl$, and the molecular weight through mass spectrometer is 508.5. $^1$H-NMR(CDCl$_3$) δ:1.15–1.27 (s, 9H, 3×CH$_3$), 1.36(m, 6H, 2×CO—OCH$_2$CH$_3$), 2.29–2.30(d, 6H,2×CH$_3$), 2.69–2.98 (m, 2H, CH2-NH), 3.46–3.76 (s, 4H,2×CO—OCH$_2$CH$_3$),3.88–4.23 (m, 2H,Ar—OCH$_2$), 4.27 (s, 1H,CH—OH), 5.21(s, 1H, Ar—CH<), 5.74 (brs, 1H, replaceable, —NH—), 6.67–7.54(m, 3H, Ar). MS m/s:508.5 (Scan FAB$^+$) Anal. ($C_{26}H_{37}O_6N_2Cl$)C,H,N. In accordance to the analytical data obtained from chemical experiments, compound 4 was found to be 4-{{2-[2-hydroxy-3-(tert-butylamino)propoxy]-5-choloro }phenyl }}-2,6-dimethyl-3,5-dicarbo-ethoxy-1,4-dihydropyridine.

EXAMPLE 5

Synthesis of Compound 5

8 gm of sodium hydroxide was dissolved in 100 ml absolute alcohol. 1 molar of 5-chlorosalicylaldehyde was dissolved in the above mentioned solution. This solution was stirred under room temperature, and 5 molar of epichlorohydrin added to react. TLC was used to determine whether the reaction was completed. After decompressed to concentrate, the concentrated solution was purified by silica gel column chromatography, eluated by hexane:ethylacetate=1:9, and concentrated to afford white coarse crystal, which was re-crystallized by hexane to obtain N-[2-(2,3-epoxypropoxy)-5-chloro]-1-benzaldehyde.

Similar molar of N-[2-(2,3-epoxypropoxy)-5-chloro]-1-benzaldehyde and 2-methyl-1-oxyethylaminobenzene were dissolved in 100 ml of absolute alcohol, and undergone amination in slight warmth. The reaction solution was concentrated under reduced pressure and purified by silica gel column chromatography (eluated by methanol:ethylacetate=1:1). The eluated solution was concentrated to obtain white solid crystal, and then re-crystallized by methanol to afford N-{2-[2-hydroxy-3-(n-butylamine)propoxy]-5-chloro}-1-benzaldehyde.

0.01M of N-{2-[2-hydroxy-3-(n-butylamine)propoxy]-5-chloro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the solution obtained was directly decompressed to concentrate and led ethanol removed. 50 ml of saturated $Na_2CO_3$ solution was then added to the remaining solution and the organic layers were extracted by $CHCl_3$ and water for several times. All the organic layers obtained were dehydrated by magnesium sulfate anhydride, filtered and concentrated, then the oil layer obtained was added to a ethanol-HCl mixed solution, purified by silica gel column chromatography, eluated by methanol:ethylacetate=3:7. Obtained eluate solution was concentrated under reduced pressure and precipitated out pale yellowish white crystals by ethylacetate, then re-crystallized by ethanol:ethylacetate=1:9 to afford compound 5.

The structure of compound obtained, compound 5 is $C_{26}H_{37}O_6N_2Cl$, and the molecular weight through mass spectrometer is 508.5. $^1$H-NMR($CDCl_3$) δ:1.11–1.22(m, 7H,N—$CH_2CH_2CH_2CH_3$), 1.22–1.29(m, 6H, 2×CO—$OCH_2CH_3$), 2.04(s, 6H, 2×$CH_3$), 2.17–2.71(m, 4H, $CH_2$—NH—$CH_2$), 3.4 (m, 4H,2×CO—$OCH_2CH_3$), 3.97–4.14(m, 2H, Ar—$OCH_2$), 4.3–4.5(m, 1H,CH—OH), 5.33(s, 1H, Ar—CH<), 6.65–7.27(m, 3H, Ar). MS m/s:508.5(Scan FAB$^+$) Anal. ($C_{26}H_{37}O_6N_2Cl$)C,H,N. In accordance to the analytical data obtained from chemical experiments, compound 5 was found to be 4-{{2-[2-hydroxy-3-(n-butylamine)propoxy]-5-choloro }phenyl }}-2,6-dimethyl-3,5-dicarbo-ethoxy-1,4-dihydropyridine.

EXAMPLE 6

Synthesis of Compound 6

8 gm of sodium hydroxide was dissolved in 100 ml absolute alcohol. 1 molar of 5-chlorosalicylaldehyde was dissolved in the above mentioned solution. This solution was stirred under room temperature, and 5 molar of epichlorohydrin added to react. TLC was used to determine that the reaction had been completed. After decompressed to concentrate, the solution was purified by silica gel column chromatography, eluated by hexane:ethylacetate=1:9 The eluated solution was concentrated under reduced pressure to obtain white coarse crystal, which was then re-crystallized by hexane to obtain N-[2-(2,3-epoxypropoxy)-5-chloro]-1-benzaldehyde.

Similar molar of N-[2-(2,3-epoxypropoxy)-5-chloro]-1-benzaldehyde and 2-methoxy-1-oxyethylamiao-benzene were dissolved in 100 ml of absolute, and undergone amination in slight warmth. Following silica gel column chromatography (eluated by methanol:ethylacetate=1:1) to purify, the eluated solution was concentrated to obtain white solid crystal and then re-crystallized by methanol to afford N-{2-[2-hydroxy-3-(2-methoxy-1-oxyethylamio-benzene) propoxy]-5-chloro}-1-benzaldehyde.

0.01 M of N-{2-[2-hydroxy-3-(2-methoxy-1-oxyethylamio-benzene)propoxy]-5-chloro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the solution obtained was directly decompressed to concentrate and ethanol removed. 50 ml of saturated $Na_2CO_3$ solution was added to the remaining solution and the E organic layers were extracted by $CHCl_3$ and water for several times. All the organic layers obtained were dehydrated, filtered and concentrated, then the oil layer obtained was added to a ethanol-HCl mixed solution, and purified by column chromatography (eluated by methanol:ethylacetate=3:7). Obtained eluated solution was concentrated under reduced pressure and precipitated out pale yellowish white crystals by ethylacetate, and re-crystallized by ethanol:ethylacetate=1:9 to obtain compound 6.

The structure of compound obtained, compound 6 is $C_{31}H_{39}O_8N_2Cl$, and the molecular weight through mass spectrometer is 602.5. $^1$H-NMR($CDCl_3$) δ:1.17–1.28(m, 6H, 2×CO—$OCH_2CH_3$), 2.27–2.29(m, 6H, 2×$CH_3$), 2.50–2.89(m, 4H, $CH_2$—NH—$CH_2$), 3.67–3.77(m, 4H, 2×CO—$OCH_2CH_3$), 3.84 (s, 3H, $OCH_3$), 3.9–4.14(m, 4H, 2×Ar—$OCH_2$), 4.26–4.33(m, 1H,CH—OH), 5.3 (s, 1H, Ar—CH<), 5.6 (brs, 1H, replaceable,—NH—). MS m/s:602.5(Scan FAB$^+$) Anal. ($C_{31}H_{39}O_8N_2Cl$) C,H,N. In accordance to the analytical data obtained from chemical experiments, compound 6 was found to be 4-{{2-[2-hydroxy-3-(2-methoxy-1-oxyethylamino-benzene) propoxy]-5-choloro}phenyl}}-2,6-dimethyl-3,5-dicarbo-ethoxy-1,4-dihydropyridine.

EXAMPLE 7

Synthesis of Compound 7

8 gm of sodium hydroxide was dissolved in 100 ml absolute alcohol. 1 molar of 2-chloro-4-hydroxy-benzaldehyde was dissolved in the above mentioned solution. This solution was stirred under room temperature, and 5 molar of epichlorohydrin added to react. TLC was used to determine that the reaction had been completed. After decompressed to concentrate, the solution was separated by silica gel column, with hexane:ethylacetate=1:9 as the eluent solution. A white coarse crystal was obtained. With repeated re-crystallization by hexane to obtain purified N-[4-(2,3-epoxypropoxy)-2-chloro]-1-benzaldehyde.

Similar molar of N-[4-(2,3-epoxypropoxy)-2-chloro]-1-benzaldehyde and 2-methoxy-1-oxyethylaminobenzene were dissolved in 100 ml of absolute alcohol, and undergone amination in slight warmth. After stirring and left to rest overnight, a white solid crystal could be obtained. Using methanol to re-crystallize, purified compound N-{4-[2-hydroxy-3-(2-methoxy-1-oxyethyl-aminobenzene) propoxy]-2-chloro}-1-benzaldehyde was obtained.

0.01M of N-{4-[2-hydroxy-3-(2-methoxy-1-oxyethylaminobenzene)propoxy]-2-chloro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the solution obtained was directly decompressed to concentrate and ethanol removed. 50 ml of saturated $Na_2CO_3$ solution was added to the remaining solution and the organic layers were extracted by $CHCl_3$ for several times. All the organic layers obtained were dehydrated; filtered and concentrated, then the oil layer obtained was added to a ethanol-HCl mixed solution, purified by silica gel column chromatography (eluated by methanol:ethylacetate 3:7), concentrated under reduced pressure, and precipitated out pale yellowish white crystals by ethylacetate, then re-crystallized by ethanol:ethylacetate=1:9 to obtain compound 7.

The structure of compound obtained, compound 7 is $C_{31}H_{39}O_8N_2Cl$, and the molecular weight through mass spectrometer is 602.5. $^1$H-NMR($CDCl_3$) δ:1.21–1.29(m, 6H, 2×CO—$OCH_2CH_3$), 2.04(m, 6H, 2×$CH_3$), 2.29–2.50

(m, 4H, CH$_2$—NH—CH$_2$), 3.82–3.86(m, 4H, 2×CO—OCH$_2$CH$_3$), 3.87–3.98 (s, 3H, OCH$_3$), 4.06–4.24(m, 4H, 2×Ar—OCH$_2$), 4.6(m, 1H,CH—OH), 5.31 (s, 1H, Ar—CH<), 5.75(brs, 1H, replaceable,—NH—). MS m/s:602.5(Scan FAB$^+$) Anal. (C$_{31}$H$_{39}$O$_8$N$_2$Cl) C,H,N. In accordance to the analytical data obtained from chemical experiments, compound 7 was found to be 4-{{N-{4-[2-hydroxy-3-(2-methoxy-1-oxyethyl-aminobenzene)propoxy]-3-choloro}phenyl}}-2,6-dimethyl-3,5-dicarbo-ethoxy-1,4-dihydropyridine.

EXAMPLE 8

Synthesis of Compound 8

8 gm of sodium hydroxide was dissolved in 100 ml absolute alcohol. 1 molar of 5-nitrosalicylaldehyde was dissolved in the NaOH solution described as above. This solution was stirred under room temperature, and 5 molar of epichlorohydrin added to react. TLC was used to determine that the reaction had been completed. After decompressed to concentrate, the solution was separated by silica gel column, with hexane:ethylacetate=1:9 as the eluent solution. A white coarse crystal was obtained. With repeated re-crystallization by hexane to obtain N-[2-(2,3-epoxypropoxy)-5-nitro]-1-benzaldehyde.

Similar molar of N-[2-(2,3-epoxypropoxy)-5-nitro]-1-benzaldehyde and tert-butylamine were dissolved in 100 ml of absolute alcohol, and undergone amination in slight warmth, purified by silica gel column chromatography, eluated by methanol:ethylacetate=1:1, concentrated under reduced pressure to obtain white solid crystal, and re-crystallized by methanol to afford compound N-{2-[2-hydroxy-3-(tret-butylamino)propoxy]-5-nitro}-1-benzaldehyde.

0.01M of N-{2-[2-hydroxy-3-(tert-butylamino)propoxy]-5-nitro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the solution obtained was directly decompressed to concentrate and ethanol removed. 50 ml of saturated NaCO$_3$ solution was added to the remaining solution and the organic layers were extracted by CHCl$_3$ and water for several times. All the organic layers obtained were dehydrated; filtered and concentrated, then the oil layer obtained was added to a ethanol-HCl mixed solution, purified by silica gel column chromatography, eluated by methanol:ethylacetate=3:7, concentrated under reduced pressure, and precipitated out pale yellowish white crystals by ethylacetate, then re-crystallized by ethanol:ethylacetate=1:9 to obtain compound 8.

The structure of compound 8 is C$_{26}$H$_{37}$O$_8$N$_3$ and the molecular weight through mass spectrometer is 519. $^1$H-NMR(CDCl$_3$) δ:1.14–1.16(s, 9H,3×CH$_3$), 1.17–1.24(m, 6H, 2×CO—OCH$_2$CH$_3$), 2.05(d, 6H, 2×CH$_3$), 2.33–2.34(m, 4H, CH2—NH), 2.85–2.98 (s, 4H, 2×CO—OCH$_2$CH$_3$), 3.98–4.17(m, 2H, Ar—OCH$_2$), 4.24–4.26(s,1H,CH—OH), 5.39 (s, 1H, Ar—CH<), 6.82–8.14(m, 3H, Ar). MS m/s: 519(Scan FAB$^+$) Anal. (C$_{26}$H$_{37}$O$_8$N$_3$)C,H,N. In accordance to the analytical data, compound 8 was found to be 4-{{2-[2-hydroxy-3-(tert-butylamino)propoxy]-5-nitro}phenyl}}-2,6-dimethyl-3,5-dicarbo-ethoxy-1,4-dihydropyridine.

EXAMPLE 9

Synthesis of Compound 9

8 gm of sodium hydroxide was dissolved in 100 ml absolute alcohol. 1 molar of 5-nitrosalicylaldehyde was dissolved in the above mentioned solution. This solution was stirred under room temperature, and 5 molar of epichlorohydrin added to react. TLC was used to determine whether the reaction was completed. After decompressed to concentrate, the concentrated solution was absorbed and purified by silica gel column chromatography, using hexane:ethylacetate=1:9 as the eluent solution. The eluated solution was concentrated under reduced pressure to obtaine the white coarse crystal, then re-crystallized by hexane to afford N-[2-(2,3-epoxypropoxy)-5-nitro]-1-benzaldehyde.

Similar molar of N-[2-(2,3-epoxypropoxy)-5-nitro]-1-benzaldehyde and 2-methoxy-1-oxyethylamino benzene were dissolved in 100 ml of absolute alcohol, and undergone amination in slight warmth. After stirring and left to rest overnight, a white solid crystal could be obtained. Using methanol to re-crystallize the solid crystal, purified compound N-{2-[2-hydroxy-3-(2-methoxy-1-oxyethyl-aminobenzene)propoxy]-5-nitro}-1-benzaldehyde was obtained.

0.01M of N-{2-[2-hydroxy-3-(2-methoxy-1-oxyethylamino benzene)propoxy]-5-nitro}-1-benzaldehyde was dissolved in a solution containing 2.4 ml (0.02M) ethylacetoacetate, 15 ml ethanol and 10 ml concentrated ammonia water; heated and placed in a water bath of 55° C. for 15 hours. After the reaction, the solution obtained was directly decompressed to concentrate and ethanol removed. 50 ml of saturated Na$_2$CO$_3$ solution was added to the, remaining solution and the organic layers were extracted by CHCl$_3$ and water for several times. All the organic layers obtained were dehydrated; filtered and concentrated, then the oil layer obtained was added to a ethanol-HCl mixed solution, and purified by silica gel column chromatography (eluated by methanol:ethylacetate=3:7), concentrated under reduced pressure, and precipitated out pale yellowish white crystals by ethylacetate, then re-crystallized by ethanol:ethylacetate=1:9 to obtain purified compound 9.

The structure of compound 9 is C$_{31}$H$_{35}$O$_{10}$N$_3$ and the molecular weight through mass spectrometer is 609. $^1$H-NMR(CDCl$_3$) δ:1.14–1.28(m, 6H, 2×CO—OCH$_2$CH$_3$), 2.04(m, 6H, 2—CH$_3$), 2.22–2.33(m, 4H, CH$_2$—NH—CH$_2$), 3.40–3.60(M, 4H, 2×CO—OCH$_2$CH$_3$), 3.83–3.85 (s, 3H, OCH$_3$), 3.99–4.13(m, 4H, 2×Ar—OCH$_2$), 4.3(m, 1H,CH—OH), 5.41 (s, 1H, Ar—CH<), 6.5(brs, 1H, replaceable, —NH—), 6.82–8.12(m, 7H,Ar). MS m/s:609(Scan FAB$^+$) Anal. (C$_{31}$H$_{35}$O$_{10}$N$_3$)C,H,N. In accordance to the analytical data obtained from chemical experiments, compound 9 was found to be 4-{{2-[2-hydroxy-3-(2-methoxy-1-oxyethylaminobenzene)propoxy]-5-nitro}phenyl}}-2,6-dimethyl-3,5-dicarbo-ethoxy-1,4-dihydropyridine.

EXAMPLE 10

Synthesis of Compound 10

8 gm of sodium hydroxide was dissolved in 100 ml absolute alcohol. 1 molar of 4-hydroxy-3-methoxy-1-benzaldehyde was dissolved in NaOH solution mentioned on the above. This solution was stirred under room temperature, and according with example 3, 5 molar of epichlorohydrin was added to react under room temperature. TLC was used to determine that the reaction had been completed. Similar procedure as the example 3 mentioned, purified compound 10 will be obtained.

The structure of compound obtained, compound 10 is C$_{32}$H$_{42}$O$_9$N$_2$ and the molecular weight through mass spectrometer is 598. Compound 10 was found to be 4-{{N-{3-[2-hydroxy-3-(2-methoxy-1-oxyethylaminobenzene)

propoxy]-4-methoxy}phenyl}}-2,6-dimethyl-3,5-dicarbo-ethoxy-1,4-dihydropyridine.

What is claimed is:

1. A compound of formula I:

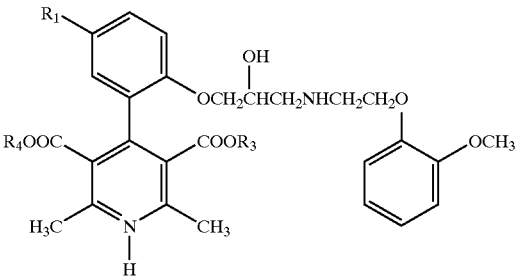

(I)

TABLE I

| Compound | Lowering of Blood Pressure (1 mg/kg; mm Hg) | Reduction of Heart Rate (1 mg/kg; beats/min) | Aorta Relaxation ($10^{-8}$M; %) |
|---|---|---|---|
| 1 | 70 ± 3 | 30 ± 2 | 30 ± 3 |
| 2 | 75 ± 2 | 35 ± 4 | 40 ± 4 |
| 3 | 78 ± 5 | 37 ± 5 | 41 ± 2 |
| 4 | 76 ± 6 | 33 ± 3 | 35 ± 5 |
| 5 | 74 ± 4 | 32 ± 4 | 33 ± 2 |
| 6 | 80 ± 3 | 35 ± 5 | 45 ± 4 |
| 7 | 82 ± 6 | 40 ± 2 | 45 ± 5 |
| 8 | 80 ± 3 | 40 ± 4 | 43 ± 3 |
| 9 | 85 ± 6 | 40 ± 5 | 47 ± 2 |

TABLE 2

| Compound | Calcium Antagonism $PKCa^{-1}$ | $\beta_1$ Value of $pA_2$ | | $\beta_2$ Value of $pA_2$ | Ratio of $\beta_1$ and Calcium Antagonism | $\beta_1/\beta_2$ |
|---|---|---|---|---|---|---|
| | | Right Atrium (Slope) | Left Atrium (Slope) | Tracheal (slope) | | |
| 1 | 7.82 ± 0.49 | 7.21 ± 0.32 (0.94 ± 0.18) | 6.91 ± 0.26 (0.85 ± 0.02) | 7.09 ± 0.54 (0.84 ± 0.09) | 0.12 | 1.32 |
| 2 | 7.91 ± 0.35 | 7.36 ± 0.65 (0.88 ± 0.09) | 6.93 ± 0.34 (0.91 ± 0.21) | 7.20 ± 0.45 (0.88 ± 0.12) | 0.09 | 1.28 |
| 3 | 7.96 ± 0.27 | 7.47 ± 0.38 (0.92 ± 0.27) | 6.97 ± 0.12 (0.89 ± 0.03) | 7.31 ± 0.23 (0.92 ± 0.23) | 0.08 | 1.26 |
| 4 | 7.94 ± 0.56 | 7.38 ± 0.12 (0.83 ± 0.12) | 6.90 ± 0.35 (0.92 ± 0.12) | 7.27 ± 0.32 (0.87 ± 0.18) | 0.08 | 1.31 |
| 5 | 7.89 ± 0.34 | 7.37 ± 0.27 (0.91 ± 0.23) | 6.91 ± 0.09 (0.93 ± 0.19) | 7.24 ± 0.12 (0.91 ± 0.21) | 0.10 | 1.33 |
| 6 | 8.01 ± 0.45 | 7.41 ± 0.34 (0.88 ± 0.12) | 7.01 ± 0.28 (0.91 ± 0.09) | 7.31 ± 0.19 (0.90 ± 0.19) | 0.11 | 1.29 |
| 7 | 8.06 ± 0.27 | 7.77 ± 0.34 (0.91 ± 0.08) | 6.97 ± 0.29 (0.88 ± 0.27) | 7.28 ± 0.21 (0.89 ± 0.21) | 0.07 | 1.34 |
| 8 | 8.09 ± 0.13 | 7.89 ± 0.23 (0.83 ± 0.21) | 7.03 ± 0.18 (0.89 ± 0.12) | 7.27 ± 0.19 (0.92 ± 0.17) | 0.08 | 1.29 |
| 9 | 8.12 ± 0.32 | 7.78 ± 0.12 (0.88 ± 0.09) | 7.12 ± 0.09 (0.91 ± 0.18) | 7.33 ± 0.24 (0.88 ± 0.23) | 0.07 | 1.30 |
| PROPRANOLOL | Not tested | 8.32 ± 0.06 (0.95 ± 0.04) | 8.23 ± 0.09 (0.81 ± 0.05) | 8.09 ± 0.12 (0.95 ± 0.08) | | 1.7 |

TABLE 3

| Compound | [$^3$H]nitrendipine $Ca^{2+}$ pKi | [$^3$H] CGP-12177 ($\beta_1$) pKi | [$^3$H] CGP-12177 ($\beta_2$) PKi |
|---|---|---|---|
| I | 7.86 ± 0.38 | 6.61 ± 0.46 | 6.20 ± 0.55 |
| Nifedipine | 8.70 ± 0.25 | NT | NT |
| PROPRANOLOL | NT | 9.12 ± 0.14 | 8.61 ± 0.1 | wherein $R_1$, $R_3$ and $R_4$ are each individually selected from the group consisting of —X, —H, —NO$_2$, CF$_3$, saturated $C_1$–$C_6$ alkyl chain, unsaturated $C_2$–$C_6$ alkyl chain, saturated $C_1$–$C_6$ alkoxy chain, and unsaturated $C_2$–$C_6$ alkoxy chain, and wherein X represents a halogen.

2. A pharmaceutical composition that comprises an effective amount of the compound of formula I of claim 1 and a pharmaceutically acceptable carrier, diluent or excipient.

3. A method for inducing hypotension or vasodilation which comprises blocking an α—, β-adrenoreceptor or calcium channel by administering to a patient in need thereof an effective amount of the composition of claim 2.

4. A method for inducing hypotension that comprises administering to a patient in need thereof an effective amount of the composition of claim 2.

5. A method for inducing vaso-relaxation that comprises administering to a patient in need thereof an effective amount of the composition of claim 2.

* * * * *